(12) United States Patent
Povey et al.

(10) Patent No.: US 6,748,815 B2
(45) Date of Patent: Jun. 15, 2004

(54) METHOD FOR DETERMINING PARTICLE SIZE

(75) Inventors: Malcolm J. W. Povey, Leeds (GB); Jie Tong, Shaanxi (CN); Phillip V Nelson, Harrogate (GB); Gregory M. Jones, Merseyside (GB)

(73) Assignee: Baker Hughes, Inc, Houston, TX (US)

( * ) Notice: Subject to any disclaimer, the term of this patent is extended or adjusted under 35 U.S.C. 154(b) by 0 days.

(21) Appl. No.: 10/282,626

(22) Filed: Oct. 29, 2002

(65) Prior Publication Data
US 2003/0084734 A1 May 8, 2003

Related U.S. Application Data

(62) Division of application No. 09/416,325, filed on Oct. 12, 1999, now Pat. No. 6,481,268.

(51) Int. Cl.[7] .......................... G01N 15/02; G01N 29/02
(52) U.S. Cl. ..................... 73/865.5; 73/61.75; 702/128
(58) Field of Search .............. 73/865.5, 61.75, 73/579, 592, 602, 607; 702/128

(56) References Cited

U.S. PATENT DOCUMENTS

| | | | |
|---|---|---|---|
| 4,283,953 A | * 8/1981 | Plona | 73/589 |
| 4,412,451 A | 11/1983 | Uusitalo et al. | 73/599 X |
| 4,509,360 A | 4/1985 | Erwin et al. | 73/599 X |
| 4,561,019 A | 12/1985 | Lizzi et al. | 73/602 X |
| 4,706,509 A | 11/1987 | Riebel | 73/825.5 |
| 4,771,470 A | 9/1988 | Geiser et al. | 382/27 |
| 4,944,189 A | 7/1990 | Nakajima et al. | 73/861.25 |
| 5,040,734 A | * 8/1991 | Belchamber et al. | 241/30 |
| 5,090,412 A | 2/1992 | Shimazaki | 73/626 X |
| 5,121,629 A | 6/1992 | Alba | 73/61.41 |
| 5,212,667 A | 5/1993 | Tomlinson, Jr. et al. | 367/7 |
| 5,339,815 A | 8/1994 | Liu et al. | 620/437 |
| 5,467,184 A | 11/1995 | Tenjimbayashi | 352/35.5 |
| 5,524,636 A | 6/1996 | Sarvazyan et al. | 73/787 X |
| 5,569,844 A | 10/1996 | Sowerby | 73/61.75 |
| 5,734,754 A | 3/1998 | Parker | 382/243 |
| 5,748,311 A | 5/1998 | Hamann et al. | 352/336 |
| 5,831,150 A | * 11/1998 | Sowerby et al. | 73/61.75 |
| 5,969,237 A | 10/1999 | Jones et al. | 73/61.75 |
| 6,109,098 A | * 8/2000 | Dukhin et al. | 73/865.5 X |
| 6,119,510 A | * 9/2000 | Carasso et al. | 73/61.75 |
| 6,205,848 B1 | * 3/2001 | Faber et al. | 73/61.75 |

FOREIGN PATENT DOCUMENTS

| | | | |
|---|---|---|---|
| EP | 0308866 A2 | 3/1989 | H01H/43/07 |
| EP | 0801305 A1 | 10/1997 | G01N/29/02 |
| SE | 509447 C2 * | 1/1999 | |
| WO | WO9919723 | 4/1999 | G01N/29/02 |

OTHER PUBLICATIONS

Abbott et al., *Acoustic Speckle: Theory and Experimental Analysis,* Ultrasonic Imaging, 1979, pp. 303–324, vol. 1, month not given.

Bamber et al., *Adaptive filtering for reduction of speckle in ultrasonic pulse–echo images,* Ultrasonics, Jan. 1986, pp. 41–44.

Behrman et al., *On–Line Ultrasonic Particle Monitoring of Brewing Operations,* MBAA Technical Quarterly, 1987, pp. 72–77, vol. 24, month not given.

(List continued on next page.)

*Primary Examiner*—Thomas P. Noland
(74) *Attorney, Agent, or Firm*—Thompson Coburn LLP

(57) ABSTRACT

The invention provides a method and an apparatus for measuring the size, concentration and size distribution of particles in a fluid by determining the characteristics of an acoustic speckle signal of the particles and relating these characteristics to the size and concentration characteristics of the particles. The method and the apparatus are especially useful for the measurement of the size distribution of small particles in optically opaque liquids.

25 Claims, 16 Drawing Sheets

OTHER PUBLICATIONS

DeBoer et al., *Screening of Crude Oils for Asphalt Precipitation: Theory, Practice, and Selection of Inhibitors,* SPE Production & Facilities, Feb. 1995, pp. 55–61.

Bouts et al., *An Evaluation of New Asphaltene Inhibitors: Laboratory Study and Field Testing,* JPT, Sep. 1995, pp. 782–787.

Niederdränk, T., *Correlations of Backscattered Ultrasound from Scattering Suspensions in Turbulent Flow,* Ultrasonics, 1995, pp. 239–242, vol. 33, No. 3, month not given.

Dickinson et al., *Ultrasonic Investigation of the Particle Size Dependence of Crystallization in n–Hexadecane–in–Water Emulsions,* Journal of Colloid and Interface Science, Mar. 1991, pp. 103–110, vol. 142, No. 1.

Holmes et al., *A Wide Bandwidth Study of Ultrasound Velocity and Attenuation in Suspensions: Comparison of Theory with Experimental Measurements,* Journal of Colloid and Interface Science, 1993, .pp. 261–268, vol. 156, month not given.

Hong et al., *Ultrasonic Speckle Pattern Correlation Interferometry Using A Pulse–Echo Method,* J. Phys. D: Appl. Phys., 1998, pp. 1392–1396, vol. 31, month not given.

Hong et al., *Considerations On Speckle Pattern Interferometry Of Ultrasonic Speckles,* Ultrasonics, 1997, pp. 329–332, vol. 35, month not given.

McClements, *Comparison Of Multiple Scattering Theories With Experimental Measurements In Emulsions,* J. Acoust. Soc. Am., Feb. 1992, pp. 849–853, vol. 91(2).

McClements, *Ultrasonic Characterisation of Emulsions and Suspensions.* Adv. of Coll. and Inter. Sci., 1991, pp. 31–72, vol. 37, month not given.

McClements et al., *Scattering Of Ultrasound By Emulsions,* J. Phys. D: Appl. Phys., 1989, pp. 38–47, vol. 22, month not given Pinfield et al., *Modeling of Concentration Profiles and UltraSound Velocity Profiles in a Creaming Emulsion: Importance of Scattering Effects,* Jrnl. of Coll. and Inter. Sci., 363–374, vol. 166, Feb. 1994.

Urick, *A Sound Velocity Method for Determining the Compressibility of Finely Divided Substances,* Jrnl. of Appl. Phys., Nov. 1947, pp. 983–987, vol. 18.

Wagner et al., *Statistics of Speckle in Ultrasound B–Scans,* IEEE Trans. on Sonics and Ultrasonics, May, 1983, pp. 156–163, vol. 30, No. 3.

Wells et al., *Speckle in Ultrasonic Imaging,* Ultrasonics, Sep. 1981, pp. 225–229.

Web Site www.agrovision.com, *Automatic Microscopy of Particle Size and Shape,* Agro Vision, accessed Mar. 16, 1999, 5 pp.

Web Site www.malvern.co.uk/labtec.htm, *Laboratory Products New Product—Mastersizer 2000 Mastersizer 2000— Taking The Alchemy Out Of Analysis,* accessed Mar. 16, 1999, 2 pp.

Web Site www.malvern.co.uk/ultra.htm, *Ultrasizer and Advantages of Ultrasound,* accessed Mar. 16, 1999, 2 pp.

Web Site www.micromeritics.com/ps—elzone—at.html, *Elzone® Analysis Technique,* accessed Oct. 15, 2002, 1 page.

Allen, *Particle Size Measurement,* Fourth Edition, Chaper 14, 1990, pp. 483–502, Chapman and Hall, London, month not given.

Berry et al., *Physical Chemistry,* 1980, pp. 1105–1109, John Wiley & Sons, New York, month not given.

Dickinson et al., *Advances in Food Colloids,* 1995, pp. 125–127, Blackie Academic and Professional, London, month not given.

Etzler et al., *Particle Size Analysis: A Comparative Study Of Various Methods,* Part. Part. Syst. Charact., 1995, pp. 217–224, vol. 12, post Jul.

McClements, *The Use of Ultrasonics for Characterising Fats and Emulsions,* Nov. 1988, pp. 43–52, Proctor Department of Food Science, University of Leeds, LS2 9JT.

Syvitski, *Principles, Methods, And Application Of Particle Size Analysis,* 1991, pp. 119–128, Cambridge University Press, Cambridge, New York, month not given.

Wellstead, P.E. *Methods and Applications of Digital Spectral Techniques,* Technical Report No. 008/83, Solatron, pp. 1–77 with Index and Preface, date unknown, but by Jun. 2000.

* cited by examiner

METHOD FOR DETERMINING PARTICLE SIZE

CROSS-REFERENCE TO RELATED APPLICATION

This application is a divisional of U.S. patent application Ser. No. 09/416,325, filed on Oct. 12, 1999 and now U.S. Pat. No. 6,481,268.

BACKGROUND OF THE INVENTION (1) Field of the Invention

The present invention relates to the measurement of size, concentration and size distribution of particles in fluids, and more particularly to the measurement of size, concentration and size distribution of particles in fluids by using acoustic speckle.

(2) Description of the Related Art

The measurement of the size and concentration of small particles in fluids is important in many industrial and diagnostic applications. Control or monitoring of operations such as crystallization, filtration, combustion, preparation of reaction feed streams, degree of reaction and the like, often depend on the ability to measure the size and concentration of small particles that are components of gas or liquid process streams.

A number of methods of measuring size and concentration of small particles are known in the art. Surveys are provided, for example, in *Principles, Methods and Application of Particle Size Analysis*, Syvitski, J., (Ed.), Cambridge University Press, London, (1991) and by Allen, T., in *Particle Size Measurement*, Chapman and Hall, London (1990).

Various optical methods that use coherent light—lasers, for example—as well as incoherent light have been reported to be useful for particle measurement in transparent or translucent fluids and in situations where particle concentration is low to moderate. Optical methods are reported that apply almost all wavelengths of light including wavelengths that are smaller, about the same as, or larger than the size of the particles to be measured. See, e.g., Etzler, et al., *Part. Part. Syst. Char.*, 12 (1995).

Other well known particle measurement techniques include phase doppler anemometry, microscopy with optical scanning and image analysis, sieving, and particle counting by optical and electrical counters. Although all of these methods are useful in certain applications, each has limitations that make it difficult or impossible to use in certain situations.

Particle measurement by the use of ultrasonic energy has been shown to have useful advantages in certain applications—for example, in streams that are optically opaque, or where particle density is high. The attenuation of sound as a function of frequency (Acoustic Attenuation Spectroscopy) has been used in the Ultrasizer™ device of Malvern Instruments Ltd., Worchester, U.K. In this method, a transducer inputs an acoustic signal having a certain frequency range into the fluid sample and a second transducer receives the attenuated portion of the original signal. Mathematical modeling permits the calculation of particle size and size distribution from the measured attenuation spectra.

Ultrasonic measurement of particles is also described by Behrman et al., *Online ultrasonic particle monitoring of brewing operations*, MBAA Tech. Quarterly, 24.72–76 (1987); Bouts et al., *An evaluation of new asphaltene inhibitors: Laboratory study and field testing*, JPT, 782–787 (1995); de Boer et al., *Screening of crude oils for asphalt precipitation: Theory, practice and the selection of inhibitors*, SPE Production & Facilities, 55–61 (1995); Dickinson et al., *Ultrasonic investigation of the particle size dependence of crystallization in n-hexadecane in water emulsions*, J. of Colloid and Interface Science, 142(1):103–110 (1991); and Holmes et al., *A wide bandwidth study of ultrasound velocity and attenuation in suspensions. Comparison of theory with experimental measurements*, J. of Colloid and Interface Science, 156:261–268 (1993); among others. U.S. Pat. No. 4,412,451 to Uusitalo et al., U.S. Pat. No. 4,509,360 to Erwin et al., U.S. Pat. No. 5,569,844 to Sowerby, and U.S. Pat. No. 4,706,509 to Riedel, also cover aspects of particle measurement by using ultrasonics.

In U.S. patent application Ser. No. 08/947,821, several of the present inventors described a novel use of ultrasonics to measure the size and concentration of small particles in fluids. In that method, a focused acoustic signal was transmitted into a fluid. Acoustic energy that is scattered by particles in the focal region of the signal is sensed by the same or another transducer. The signal of scattered ultrasonic energy is transformed from a time format to a frequency format and particle size and size distribution can be calculated by analysis of the magnitude of the signal as a function of frequency. This method was reported to be useful for the real-time measurement of particles in opaque liquids, such as crude oil.

A characteristic that has long been recognized in both laser and acoustic spectrometry is the phenomenon of "speckle". General discussions of ultrasonic speckle have been provided by Wagner et al., *Statistics of speckle in ultrasonic B-scans*, IEEE Transactions on Sonics and Ultrasonics, 30(3):156–160 (1983), and Abbott et al., *Acoustic speckle: Theory and experimental analysis*, Ultrasonic Imaging, 1:303–324 (1979).

The presence of acoustic speckle has been traditionally regarded as an annoyance in applications' such as ultrasonic medical imaging and efforts to minimize ultrasonic speckle have been reported by Wells et al., *Speckle in ultrasonic imaging*, Ultrasonics, 225–229 (September 1981), and Bamber et al., Ultrasonics, 41–44 (January 1986), and speckle minimization has been the subject of U.S. Pat. No. 4,561,019 (RE35,148) to Lizzi et al., U.S. Pat. No. 4,771,470 to Geiser et al., and U.S. Pat. No. 5,090,412 to Shimazaki.

More recently, however, there have been reports of the potential of deriving useful information from speckle patterns. See, e.g., Hong, S-K, and J-B Han, *Considerations on speckle pattern interferometry of ultrasonic speckles*, Ultrasonics, 35:329–332 (1997), for a description of the potential for using ultrasonic speckle to produce information about deformations and flaws in the internal parts of a material that can transmit ultrasonic waves. The same group report how known deformations produce changes in ultrasonic speckle patterns in Hong, S-K and Y. G. Ohr, *Ultrasonic speckle pattern correlation interferometry using a pulse-echo method*, J. Phys. D. Appl. Phys., 31:1392–1396 (1998), The use of ultrasonic speckle signals to derive information about particles in fluid systems has been described by Nakajima et al. (U.S. Pat. No. 4,944,189) who report an ultrasonic speckle velocity measurement apparatus and method. A reported advantage of the method is that it can measure fluid velocity even at low velocities and the measurement is reported to be unaffected by the number or concentration of particles in the fluid.

Despite significant improvements in the methods and instruments available to measure the size and concentration of small particles in fluids, there remain certain applications where such measurement is difficult or impossible. For example, in fluids that are optically opaque—such as crude oil—or where particle concentration is high, and where measurements are required on a rapid basis—even on a real-time basis—and without dilution of the fluid, conventional particle measurement systems are unsuitable. Accordingly, it would be useful to provide a method and an apparatus for measuring particle size, concentration and size distribution of small particles in fluids that would be suitable for use even in optically opaque fluids. It would also be useful to provide such a method and an apparatus that could provide such measurements on a rapid, or real-time basis. It would also be useful if such a method and apparatus could perform these measurements without diluting the fluid in which the particles are carried.

BRIEF SUMMARY OF THE INVENTION

Briefly, therefore, the present invention is directed to a method for determining the size of particles in a fluid comprising the steps of obtaining an acoustic speckle signal of the particles in the fluid and deriving the size of the particles in the fluid from the acoustic speckle signal.

The present invention is also directed to a novel method for measuring the concentration of particles in a fluid comprising the steps of obtaining an acoustic speckle signal of the particles in the fluid and deriving the concentration of particles in the fluid from the acoustic speckle signal.

The present invention is also directed to a novel method for determining the size distribution of particles in a fluid comprising the steps of obtaining an acoustic speckle signal of the particles in the fluid and deriving the size distribution of the particles from the acoustic speckle signal.

The present invention is also directed to a novel method for determining the degree of particle agglomeration in a liquid containing particles that produce individual speckle events, the method comprising obtaining, for two or more individual speckle events, an individual acoustic speckle signal from the liquid and determining the degree of agglomeration from the acoustic speckle signal.

The present invention is also directed to a novel apparatus for determining the size distribution of particles in a fluid comprising a signal generator capable of generating an electrical signal; a transducer that can translate the electrical signal from the signal generator into an acoustic input signal that is introduced into the fluid; a sensor that can sense acoustic energy that is scattered by the particles in the fluid in response to their interaction with the acoustic input signal and provide an output electrical signal that is related to the sensed acoustic energy; an oscilloscope that is capable of acquiring the output signal in an amplitude versus time domain and transforming the signal to a magnitude versus frequency domain; and a computer that is programmed with an algorithm that is capable of identifying an acoustic speckle signal in the frequency domain and relating the magnitude and/or duration of the acoustic speckle signal to the size distribution of the particles in the fluid.

Among the several advantages found to be achieved by the present invention, therefore, may be noted the provision of a method and an apparatus for measuring particle size, concentration and size distribution that are suitable for use even in optically opaque fluids; the provision of such a method and an apparatus that could provide such measurements on a rapid, or real-time basis; and the provision of such a method and an apparatus that could perform such measurements without diluting the fluid in which the particles are carried.

BRIEF DESCRIPTION OF THE SEVERAL VIEWS OF THE DRAWINGS

Corresponding reference characters indicate corresponding parts throughout the several views of the drawings.

DETAILED DESCRIPTION OF THE INVENTION

In accordance with the present invention, it has been discovered that the size, concentration and size distribution of small particles in a fluid can be derived from a measurement of acoustic speckle signals produced by the particles in response to input signals of acoustic energy. This surprising discovery is especially significant because acoustic speckle, particularly for energy of ultrasonic wavelengths, can be measured very quickly and can be transmitted and sensed even in optically opaque fluids. Moreover, the novel measurement technique of this invention can be used alone or can be combined with other particle measurement techniques to provide valuable knowledge about the size and concentration characteristics of both small and larger particles in a fluid on a real-time basis. The method of this invention can be used on fluid samples in a test cell or on fluids in process flow streams, in tanks or in reactors. In fact, it is believed that the method can be applied anywhere an ultrasonic transducer can be introduced into a fluid to be tested. Moreover, it is believed that the method can be applied to any fluid that will transmit ultrasonic waves and that it can be used to measure the size and concentration characteristics of any particles that scatter ultrasonic energy and that are sufficiently small that their motion within the fluid is controlled by Brownian motion.

Figure 1A:
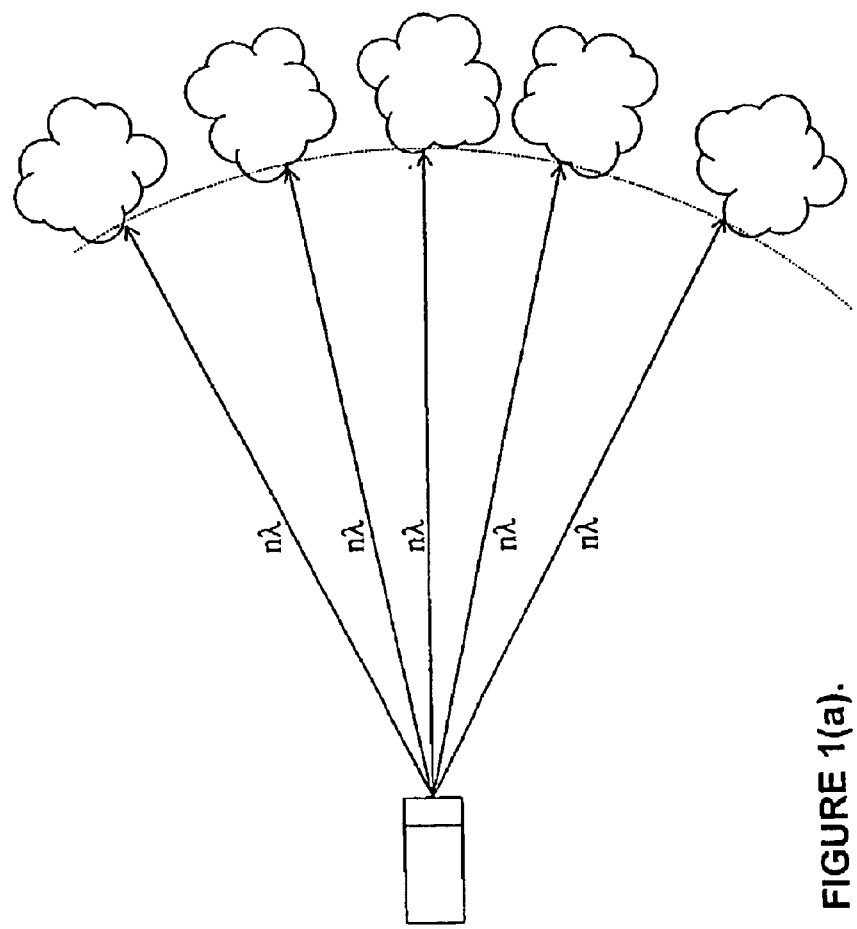
FIG. 1 shows conceptual representations of an acoustic wave signal approaching particles in a fluid that are arranged in (a) one form of an acoustic mirror, or (b) a Bragg lattice.
Figure 1B:
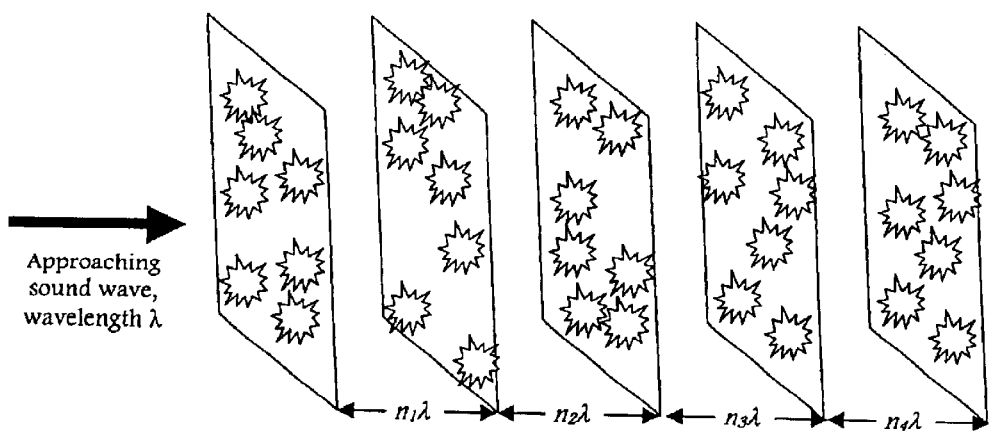

Without wishing to be bound by this or any other theory, it is believed that the production of acoustic speckle signals by small particles in a fluid is related to their tendency to move randomly with Brownian motion. When a beam of monochromatic acoustic energy having a certain wavelength and a certain diameter interacts with the particles, the particles scatter some portion of the acoustic energy. From time to time, some of these particles, each having a diameter that is less than the wavelength of the interacting beam of acoustic energy and less than the beam diameter, assemble stochastically into a common plane before moving out of formation again. Occasionally, this plane will lie orthogonal to the path of the acoustic beam and the backscattered signal from each particle will form a coherent sum at the transducer. When these criteria are satisfied, the particles are said to form an acoustic mirror, one form of which is illustrated in FIG. 1(a). A similar effect can also be produced by particles that are not in the same plane orthogonal to the propagation direction of the ultrasound signal, as long as the particles lie in planes that are separated an integral number of wavelengths apart along the path of the sound wave. Such an arrangement is termed a "Bragg lattice", as illustrated in FIG. 1(b), which also results in a coherent sum of the backscattered signal from all the particles at the transducer. Particles in either of the arrangements described above will be referred to herein as being in an acoustic mirror, or simply, a mirror.

As used herein, particles are considered to be "small particles" if their motion in a static fluid is controlled primarily by Brownian motion, as opposed to, for example, gravitational force. The diameter of such small particles is believed to be much less than the wavelength of the acoustic energy signal. For a signal having a wavelength that corresponds to a frequency of 1 MHz, for example, this would mean particles having a diameter of from about 5 micrometers down to a few nanometers.

It would also be possible for larger particles to create coherent backscattered signals that sum at the transducer as a result of mechanical stirring, convection currents, sedimentation or creaming.

For the purposes of this invention, it will be assumed that all particles and agglomerates of particles are substantially spherical particles having the same mass as the actual particle and the term "particle size", as that term is applied to single particles, is to be understood to mean a number that is proportional to the diameter of the substantially spherical particle or the agglomerate.

Figure 2A:
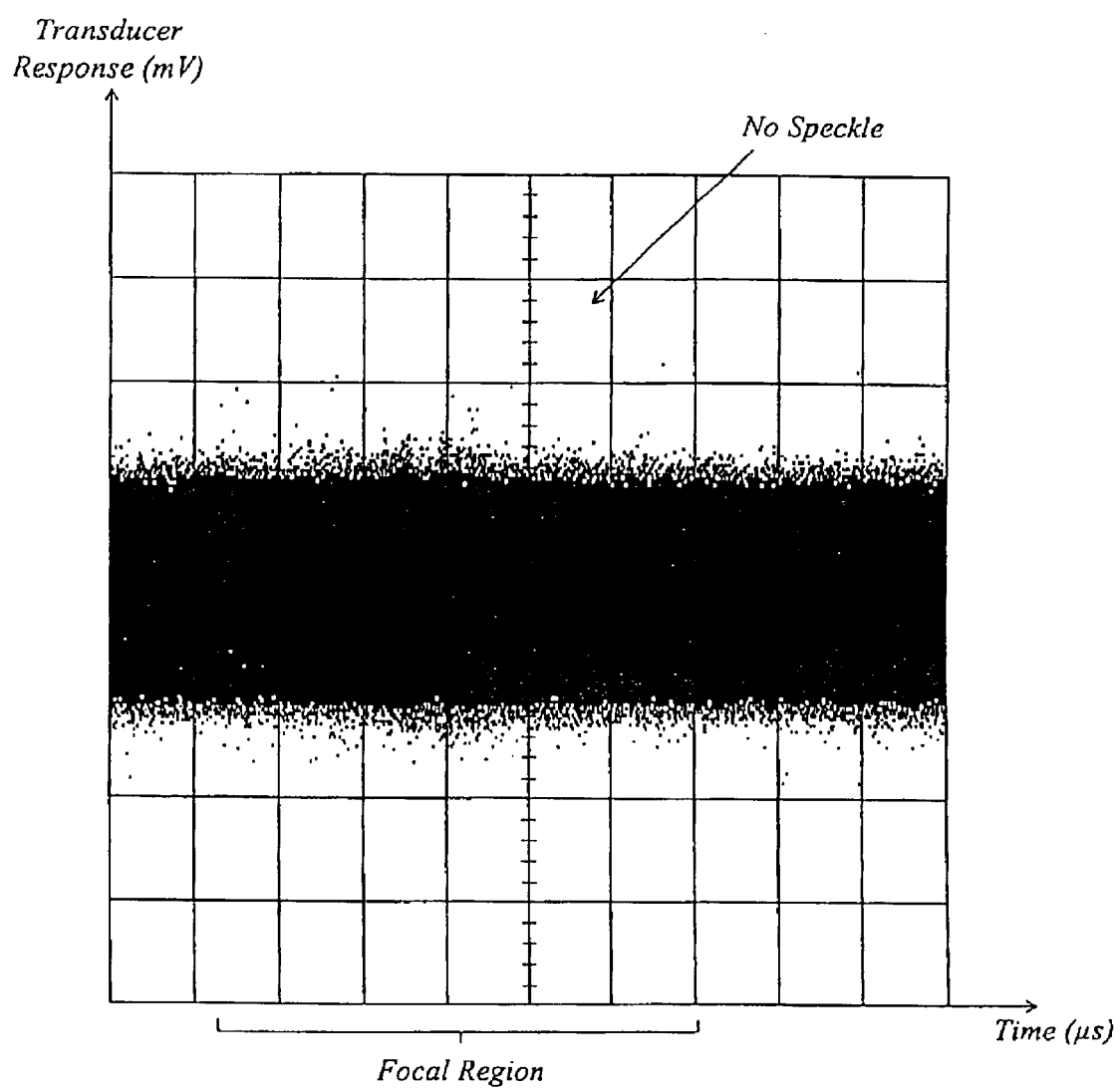
FIG. 2 shows a persistence display for over 1000 sweeps from an oscilloscope of an amplitude versus time plot of acoustic energy scattered by particles in crude oil, showing (a) no speckle; (b) several speckle events within a focal region; and (c) speckle events within and outside of a focal region.
Figure 2B:
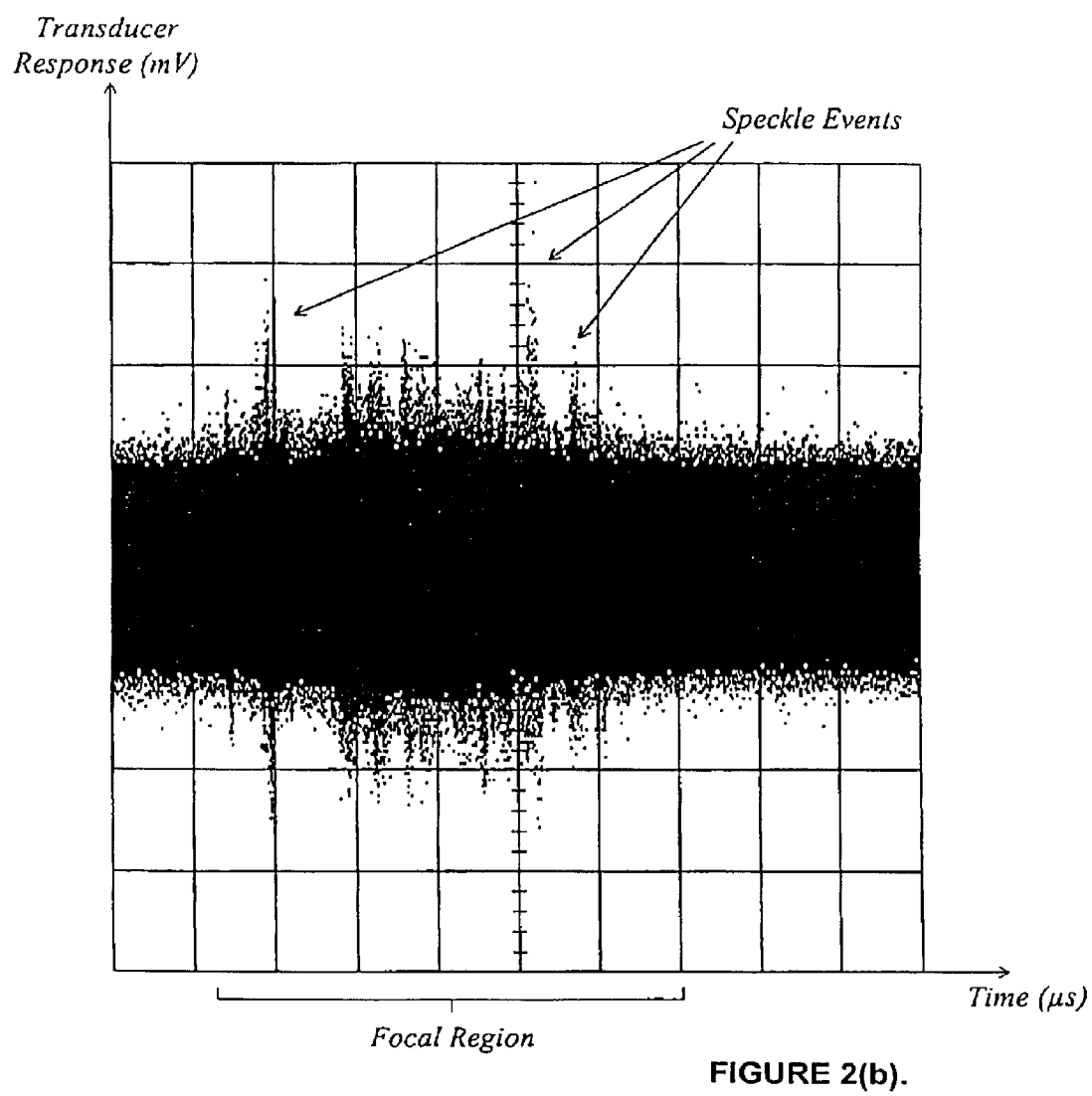
Figure 2C:
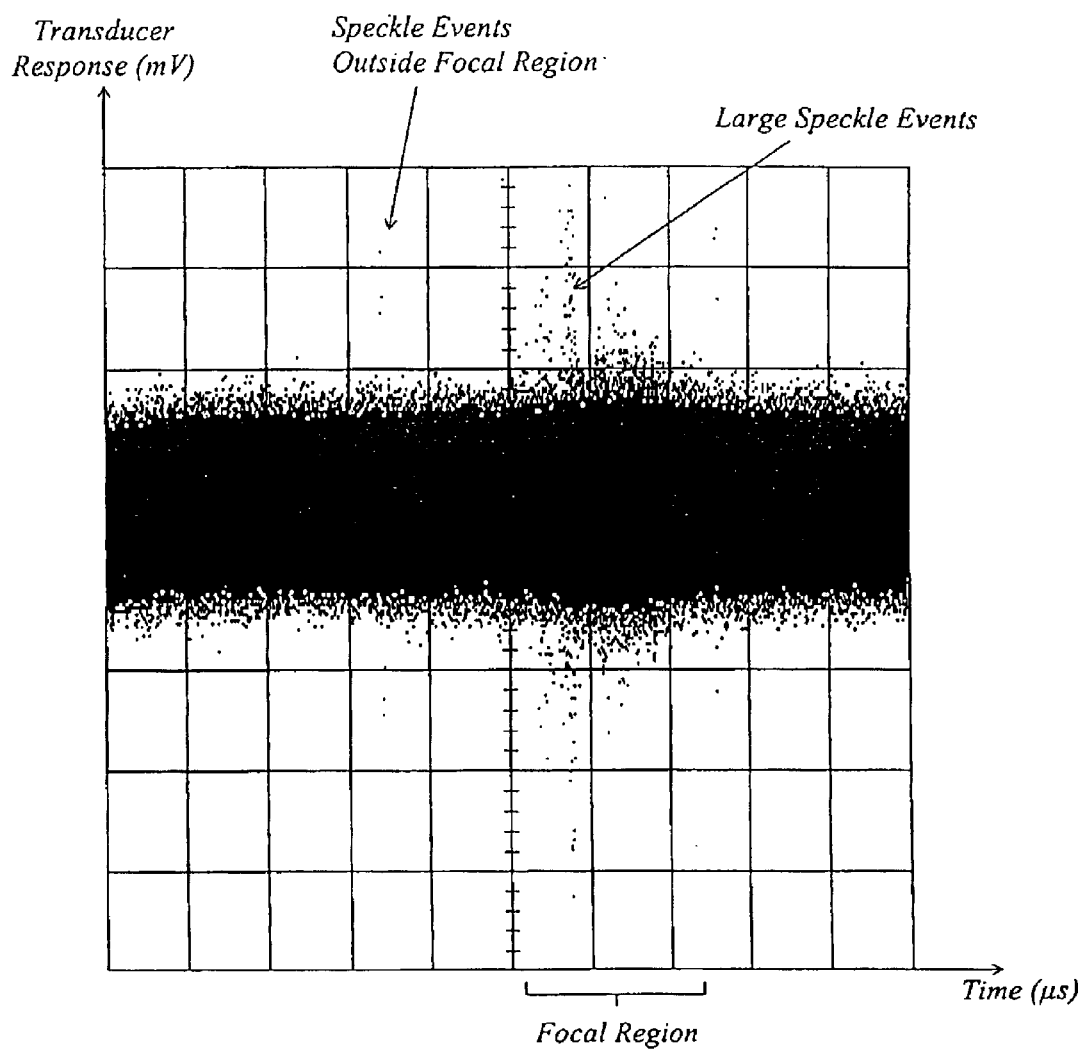

During the period that the scattering particles remain in an acoustic mirror, the approaching acoustic wave encounters each particle in the lattice at the same moment and acoustic energy is emitted by each scattering particle simultaneously and in phase. A portion of the acoustic energy that is scattered by these particles can be sensed and measured by a sensing transducer to produce an electrical signal that corresponds to the scattered acoustic energy. The acoustic emissions from the mirror combine at the sensing transducer and produce a characteristic signal that is termed an "acoustic speckle" (which, hereinafter, may also be termed a "speckle", or "speckle signal", or "speckle event"). The speckle can be displayed on an oscilloscope amplitude versus time plot of scattered ultrasonic energy as a peak having an amplitude significantly greater than that of the energy scattered by particles that are not in a mirror. Several acoustic speckle peaks can be seen in FIGS. 2(b) and 2(c) as dotted line excursions whose amplitude significantly exceeds the amplitude of non-speckle scattering.

If it is assumed that the formation and subsequent disintegration of the mirror is due to the random motion of the particles, or aggregates of particles, in the fluid, then, by measuring certain properties of the speckle signal, information can be gathered regarding the mirror itself, and the particles contained in it. Although each mirror forms and disintegrates due to the random motion of the scattering particles, the period of time for which the structure exists is dependent upon the speed with which the scattering particles move in the fluid. The velocity of small particles in a fluid due to Brownian motion depends upon the particle size and the viscosity of the fluid. In a fluid having a given viscosity, smaller, dispersed particles will move faster than their larger, or aggregated, counterparts and speckles from small particles will appear and disappear more quickly than will speckles produced by large particles or aggregates.

Figure 10:
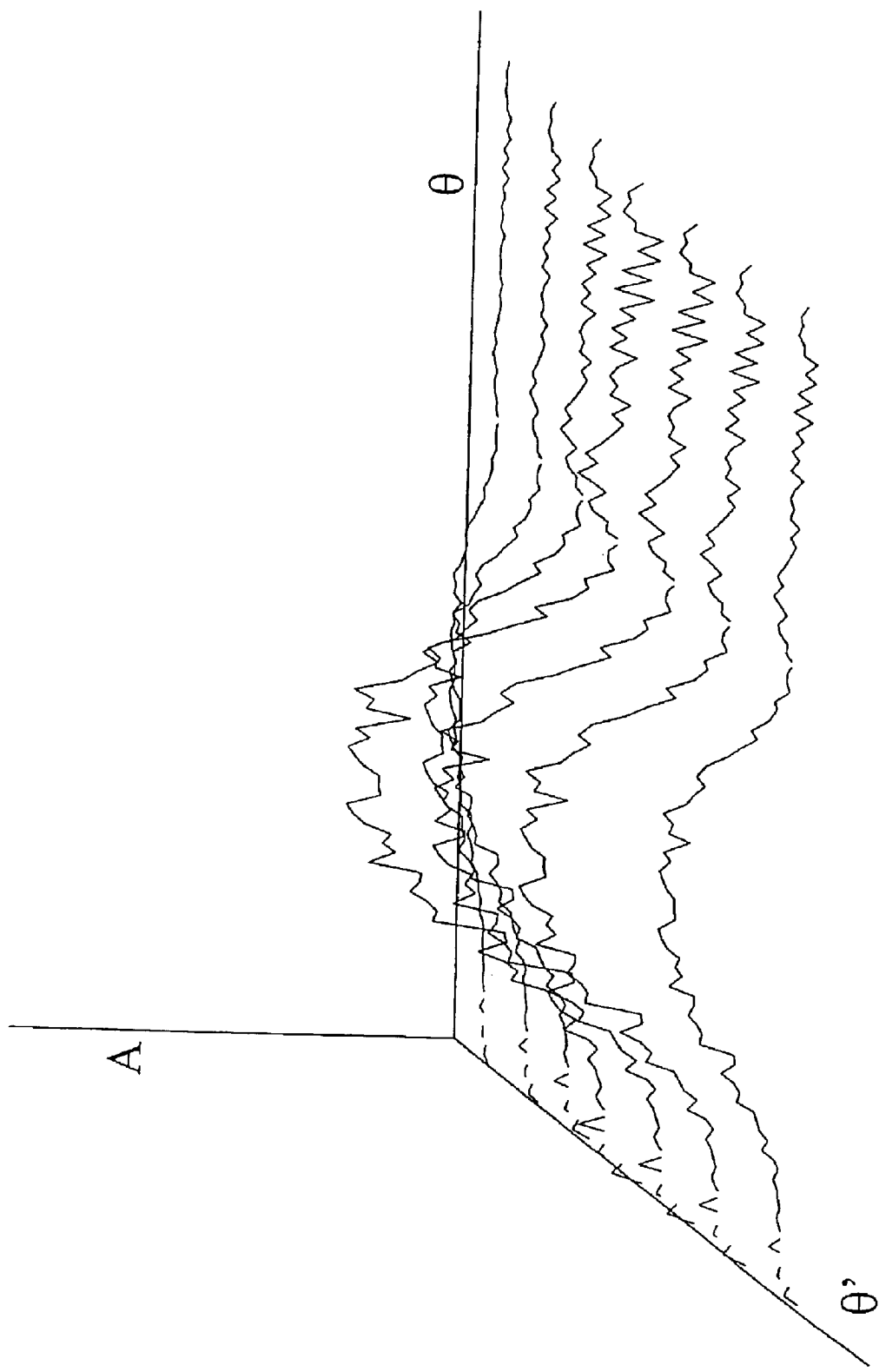
FIG. 10 shows a conceptual view of an amplitude (A) versus time (θ) plot of scattered acoustic energy where the scan has been repeated at a selected repetition frequency over a period of time along the θ' axis.
Figure 11:
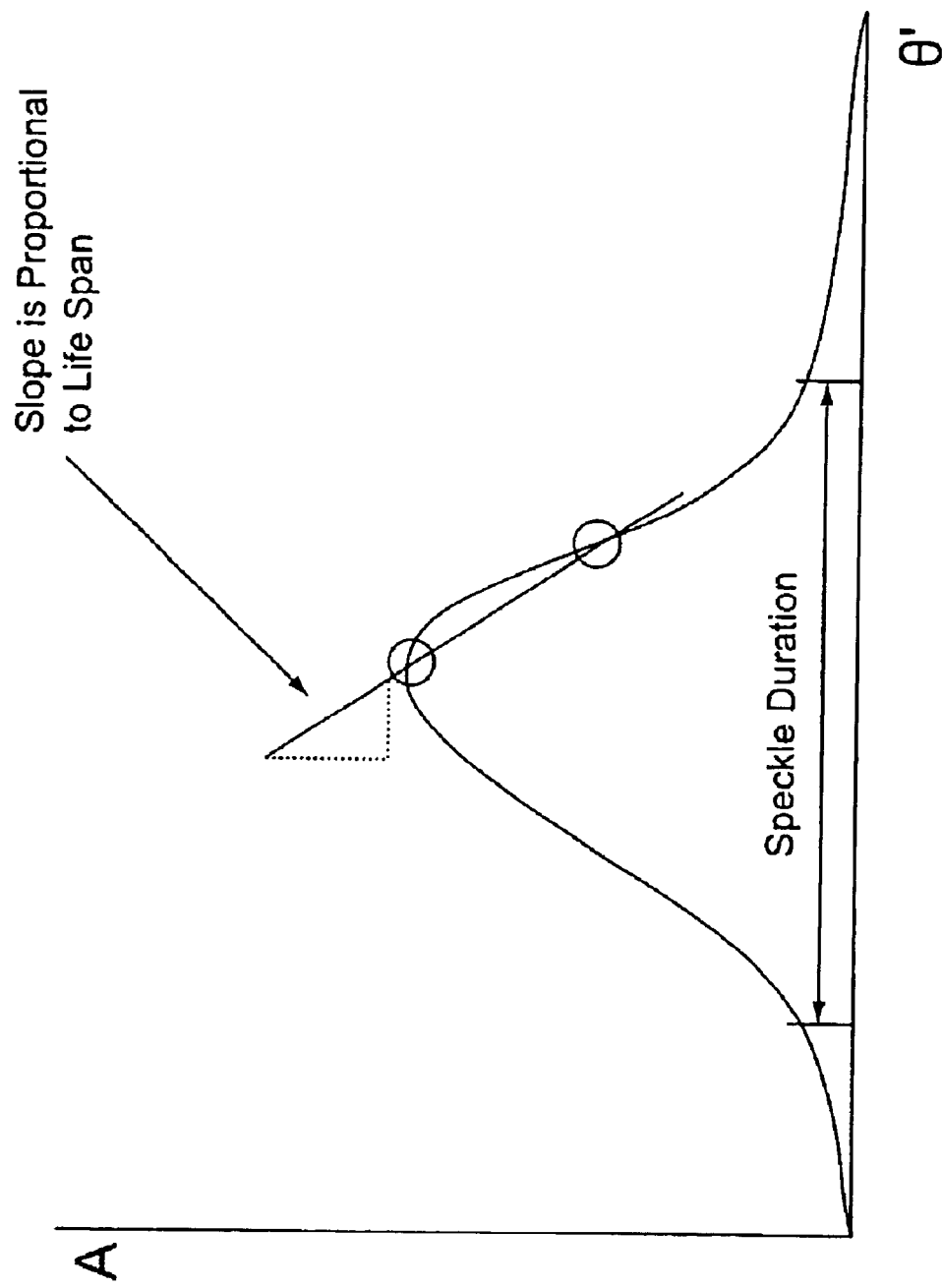
FIG. 11 is a plot of the maximum height of the peak on each of the A vs. θ plots of FIG. 10 plotted versus time (θ'), and illustrates the duration of a speckle event.

Surprisingly, it has been found that the duration of an acoustic speckle event can be used to derive the size of the particles in the mirror that produced the speckle. The duration of the acoustic speckle event represents the life span of the speckle event in time. As used herein, the term "duration" is a number that is proportional to the life span over time of a measured signal of a speckle event. Depending upon how the duration of a speckle event is measured, the measured value can be equal to the total life span of the individual signal of the speckle event, or it can be some particular fraction thereof. This concept can be described, for illustration purposes only, by reference to FIGS. 10 and 11. FIG. 10 shows a conceptual view of an amplitude (A) versus time ($\theta$) plot of scattered acoustic energy where the scan has been repeated at a selected repetition frequency over a period of time along the $\theta$' axis. During the period of time that is shown, an acoustic speckle signal is sensed and the speckle signal is shown as the peak in the A vs. $\theta$ plots. The maximum height of the peak on the A vs. $\theta$ plots can be plotted versus time ($\theta$') as shown in FIG. 11 to illustrate the duration of the speckle event.

As described above, the duration of this speckle event can be derived from either a direct measurement of the life span on the persistence display of the oscilloscope, or correlation with frequency dependent scattering amplitude via scattering theory by using techniques analogous to those employed by dynamic light scattering instrumentation such as the Malvern Zetasizer, (Malvern Zetasizer Manual, Malvern Instruments, Malvern, U.K.). Alternatively, the duration can be measured by the calculation of some parameter from the speckle signal peak that is a particular fraction of the life span—such as by calculation of an autocorrelation function as described by Berry et al., in *Physical Chemistry*, p.1106, Wiley Publ. New York (1980); and by Wellstead, P. E., *Methods and Applications of Digital Spectral Techniques*, Technical Report No. 0008/83, UMIST, Solartron Instruments, Farnborough, U.K. Such an approach is illustrated in FIG. 11 by the straight line passing through the maximum of the peak and through the curve at a selected later point. The slope of the line can be used to derive the duration, since it can be related to the life span of the speckle event.

It is believed that a particle size derived from the duration of a speckle signal by any of these methods represents an average of the sizes of the particles that produced the speckle signal. When the term "particle size" is used herein, it is to be understood to include absolute particle size, as well as values that are related to absolute particle size and from which the absolute particle size can be derived.

It also has been found, surprisingly, that a measurement of the frequency of occurrence of acoustic speckle events can be used to derive the concentration of particles in the fluid. It is believed that there is a direct correlation between the concentration of the particles in the fluid and the number of speckle events that occur per unit time. The higher the particle concentration in the fluid, the more frequent the particles form a mirror and, thus, produce an acoustic speckle event.

Furthermore, it has been found that the size distribution of the particles in the fluid can be derived from a measurement of the number and duration of speckle events over a sufficient period of time. This derivation is possible because the average size of the particles producing each speckle event can be derived from the duration of the individual speckle signal and, thus, the frequency of occurrence of speckle events for an array of average particle sizes essentially represents the particle size distribution of the particles in the fluid. Since the measurement of speckle duration provides an average particle size, it is believed that the more speckle events that are included in the calculation, the more accurate will be the particle size distribution that is derived in this manner.

Also, it has been found, surprisingly, that the peak height of an acoustic speckle signal is related to the total cross-section area of the particles that produced the speckle event. This provides the basis for an alternative method of deriving particle concentration. The method can be briefly described as follows. Since the average size of the particles producing the speckle event can be derived from the duration of the speckle signal—as described above—the number of particles that produced the speckle can be derived by dividing the total cross section area of particles producing the speckle by some function of the average particle diameter. This number can be used to produce a particle concentration value when it is related to some characteristic volume, such as, for example, the volume of the focal region of the transducer, as will be described below. Once particle concentration is determined, the size distribution of the particles in the fluid can be derived by a method that is similar to that described above.

Figure 3:
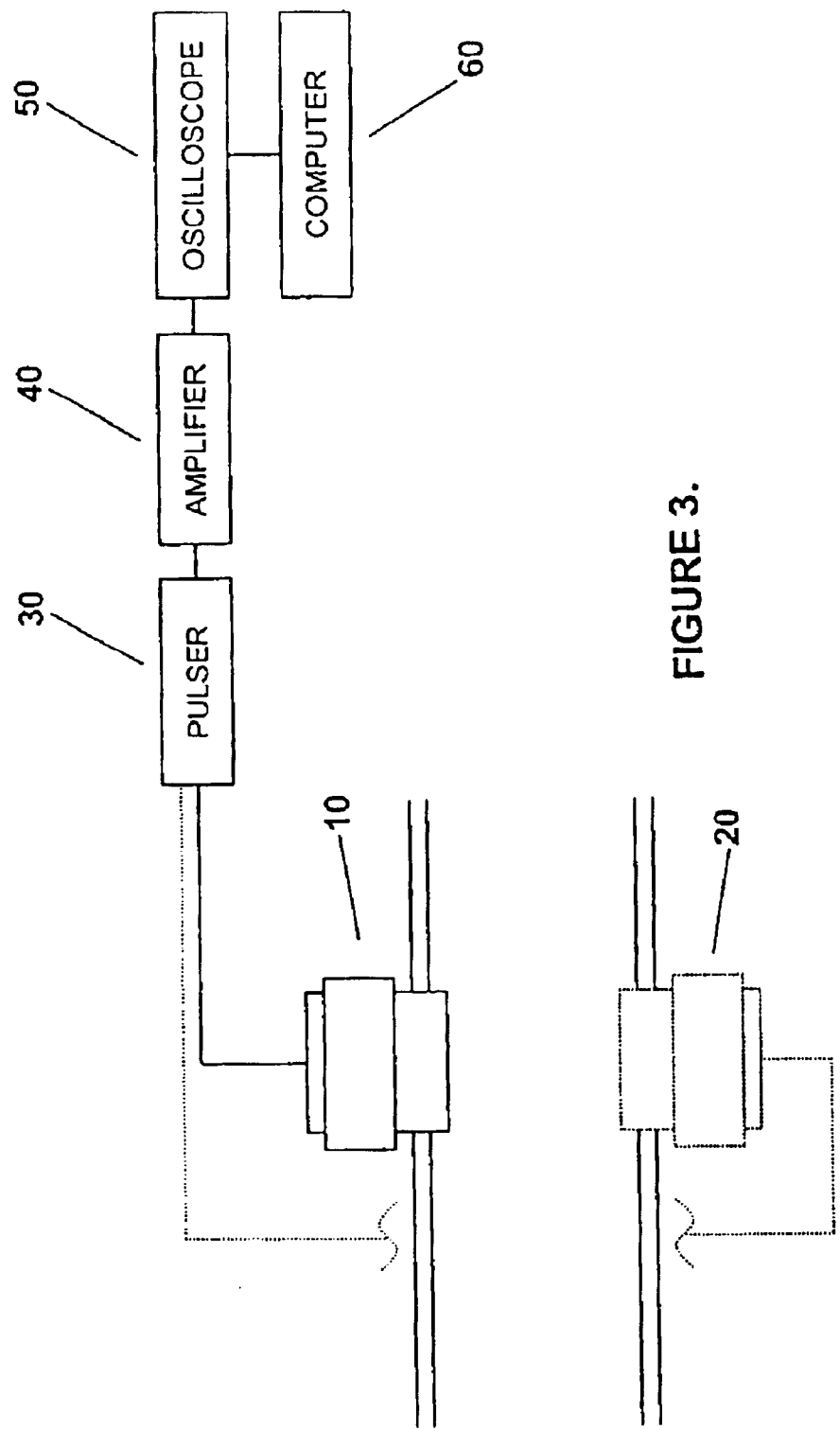
FIG. 3 is a block diagram of one embodiment of an apparatus suitable for practicing the present invention showing the arrangement of components.

Apparatus:

A system that may be used to practice the present invention is shown in FIG. 3. In general, a signal generator, or pulser 30, generates an electrical signal which is transmitted to a transducer 10 that transduces the electric signal into an acoustic input signal that is introduced into the fluid having the particles to be measured. The same transducer, or, optionally, a separate transducer, acts as a sensor 20, to sense a portion of the acoustic energy that is scattered by the particles in the fluid in response to their interaction with the acoustic input signal and provide an output electrical signal that corresponds to the sensed acoustic energy. An amplifier 40 amplifies the output signal and transmits the amplified signal to an oscilloscope 50 that is capable of acquiring the output signal in an amplitude versus time domain and transforming the signal to a magnitude versus frequency domain. If the transducer has a focal lens that focuses the input signal on a focal region in the fluid, the oscilloscope is preferably capable of selecting that part of the detected scattered signal that results from acoustic scattering by particles in the focal region (which step can be termed "gating") and transforming only the selected part of the output signal into a magnitude vs. frequency domain. This transformed output signal can be transmitted to a computer 60 that is programmed with an algorithm that is capable of relating the magnitude and/or duration of the acoustic speckle signals to the size of the particles in the fluid.

As would be readily recognized by one of ordinary skill in the art of ultrasonic measurement, the system described above could be easily modified while still carrying out the same functions. For example, the electric signal to be transmitted to the transducer 10 could be generated by a combined pulser/amplifier, as well as by the pulser 30. Alternatively, the oscilloscope 50 could provide amplification of the sensed signal and replace the separate amplifier 40. Likewise, if desired, the computer 60 could accomplish the calculation functions ascribed above to the oscilloscope 50, or vice versa. The acoustic transducer 10 may be mounted in a test cell, or may be mounted directly in a pipeline or a tank. Other systems for the ultrasonic measurement of particles in liquids are generally described in U.S. Pat. No. 4,412,451 to Uusitalo et al., U.S. Pat. No. 4,509,360 to Erwin et al., U.S. Pat. No. 4,706,509 to Riebel, and U.S. Pat. No. 5,121,629 to Alba.

The various parts of a system to practice the present invention and their operation are described as follows.

Figure 4:
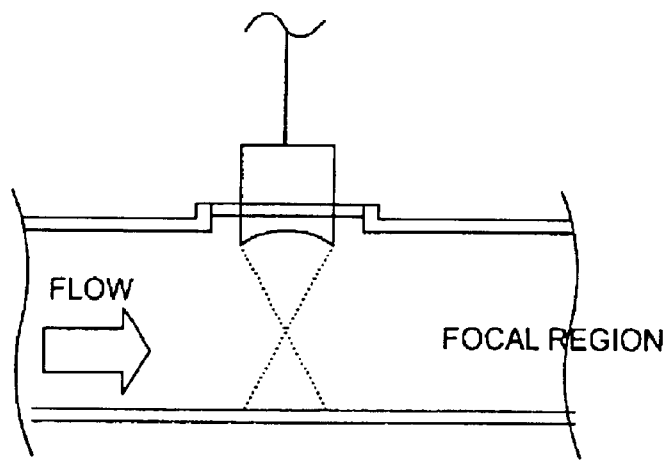
FIG. 4 shows a representation of a cross-sectional view of a focused transducer of the present invention mounted in a pipe containing a flowing fluid and indicating the convergence of the acoustic signal into a focal region within the fluid.

The transducer 10 is an ultrasonic transducer that introduces a signal of acoustic energy into the fluid. The transducer includes, in general, a piezoelectric element capable of transforming electrical signals into physical pulses. If the element is in contact with a fluid, such physical pulses are transferred to the fluid and initiate waves having a frequency that is controlled by the frequency of the electronic signal. Preferably, the transducer 10 is a focused transducer that contains a lens to focus the signal as illustrated by the dashed lines of FIG. 4. The focal length of the transducer is the distance from the end of the transducer to the point where the wave patterns converge. Focal length may be estimated as:

$$\text{Focal length} = R(C_1)/C_1 - C_m)$$

where: R is the radius of the lens of the transducer; $C_1$ is the speed of sound in the lens; and $C_m$ is the speed of sound in the probed medium.

While focal length is not critical, it is preferred that the focal length is less than the distance from the lens of the transducer 10 to any solid material or to the opposing wall of a test cell, pipe or tank. In other words, the focal region should be within the fluid of interest. A transducer 10 having a focal length of about 100 mm to about 200 mm is suitable for the present invention as long as no wall, pipe or other process equipment structure intervenes between the transducer 10 and the focal region.

The selection of a transducer 10 involves consideration of its capability to introduce into the fluid an acoustic signal with respect to the characteristics of duration, power and frequency. Such signal can be in the form of a pulse that is transmitted to the transducer 10 as a high-voltage spike of short duration and typically repeated many times per second, or as a tone burst. Although the use of pulse signals is preferred, tone burst signals are useful in circumstances where the use of high voltage is undesirable and where a signal of narrower frequency band is preferred. The voltage of the input signal pulse can be from about 100 to about 600 volts. An input signal pulse voltage of from about 200 to about 500 volts is preferred and from about 250 to about 500 volts is more preferred.

The input signal is transmitted to the transducer at a pulse repetition frequency of from about 5 to about 250 Hertz (Hz). However, a frequency of from about 20 to about 200 Hz is preferred and a frequency of from about 100 to about 200 Hz is more preferred.

The duration of the input signal can be from about 5 to about 80 nanoseconds (ns). However, it is preferred that the duration of the input signal be from about 10 to about 60 ns and it is more preferred that the duration be from about 20 to about 40 ns.

The detected power of the input signal can be amplified so that it is from about 5 to about 50 decibels (dB). However, it is preferred that it be from about 10 to about 40 dB and more preferred that it be from about 20 to about 40 dB.

By way of example, a series of input pulses, each of 500 volts, having a duration of 25 nanoseconds and a power of 33 dB and repeated at a frequency of 200 Hz, and with a receiver gain of 33 dB, is suitable for some applications of this invention.

Typical operation of an acoustic transducer and ultrasonic systems similar to those suitable for use in the present invention is described, for example, by Urick, R. J.,*J. Appl. Phys,* 18, 983–987 (1947); McClements, D. J., et al.,*J. Phys. D: Appl. Phys,* 22, 38–47 (1989); Holmes, A. K., et al., *J. Coll. Int. Sci,* 156, 261–268 (1993); McClements, D. J.,*Adv. Coll. Int. Sci,* 37, 33–72 (1991); McClements, D. J., *J. Acoust. Soc. Am,* 91, 849–853 (1992); Pinfield, V. J., et al., *J. Coll. Int. Sci,* 166, 363–374 (1994) and McClements, D. J., *The use of ultrasonics for characterizing fats and emulsions*, Ph.D. Thesis, Food Science Department, University of Leeds, UK (1988).

The transducer should be capable of resisting temperature to 200° C., and preferably to 300° C., and most preferably to 500° C. The transducer should also be capable of resisting pressure to about 200 kPa, and preferably to about 2.50 MPa and most preferably to about 5 MPa. Moreover, the transducer should preferably be capable of resisting chemical corrosion and physical erosion by the fluids in which it is to be used.

Suitable transducers may be commercially obtained or may be constructed. One type of commercially available acoustic transducer suitable for use in the present system is a SLIM 10-10/SF30 mm/834/02, 10 MHz transducer as supplied by Sonatest Ltd., Milton Keynes, U.K.

The acoustic transducer 10 may also be used as a sensor to sense acoustic energy scattered by particles in the fluid. Alternately, a separate sensor 20 may be used. If a separate sensor 20 is used, it may be placed anywhere in the fluid in relationship to the probe 10, that is insensitive to the directly transmitted beam, but is preferably close enough to receive energy scattered from the focal region. The sensor, whether the transducer 10, or a separate sensor 20, converts that portion of the scattered acoustic energy encountering the piezoelectric element into an electrical signal. This signal corresponds to the amplitude of the portion of scattered acoustic energy encountering the piezoelectric element as a function of time and is termed the "output signal". Operation of an acoustic energy sensor, in general, is described by the references given above in the section describing the transducer 10.

It is preferred that the sensor of the subject system has sensitivity suitable for sensing back-scattered energy having frequencies up to 20 MHz, but a sensor which can sense back-scattered energy having frequencies up to 100 MHz is more preferred and a sensor which can sense back-scattered energy having frequencies up to 200 MHz is most preferred.

A pulser/receiver, or pulser 30 provides the necessary input signal to drive the transducer 10. An amplifier 40 amplifies the sensed scattered signal before it is transmitted to the oscilloscope 50. The pulser 30 and amplifier 40 may be separate components or may be combined in a single component. For example, a pulser/receiver that provides both pulser 30 and amplifier 40 functions in a combined component is a UTEX 320; available from Scientific Instruments Inc., Mississauqua, Ontario, Canada. It is preferred that the pulser/receiver is supplied with a software package such as, for example, Ultrasonic Instrument Control V3.04. The pulser/receiver is capable of providing an input signal having a frequency range of 1 MHz to 150 MHz; a pulse voltage of from 100 V to 500 V; a pulse width of from 5 ns to 80 ns; a pulse repetition frequency (PRF) of about 200 Hz to 20 KHz; and a gain of from 0 to 63 dB The oscilloscope 50 of the present system should be capable of gating the scattered acoustic signal by limiting the output signal to the portion of acoustic energy scattered by particles in the focal region. The oscilloscope is also preferably capable of carrying out an analog-to-digital conversion and, more preferably, of transforming the output signal from an amplitude vs. time domain to a magnitude vs. frequency domain as described below. The gating function limits the output signal to the sensed energy that was scattered by particles within the focal region. Thus, the gating step deletes that part of the signal caused by any reflection due to an opposing pipe wall and all other portions of the signal except for the scatter due to particles in the focal region.

An oscilloscope that is suitable for use in the present system is, for example, a LeCroy 9310A, dual channel 400 MHz oscilloscope, with a sampling rate up to 100 MS/s. Such oscilloscopes should be complete with software suitable for waveform processing such as, for example, Wave form processing packages WPO1 and WPO2 incorporating FFT averaging function, available from LeCroy.

Data from the oscilloscope is transferred to a computer 60 by using, for example, a National Instruments IEEE Plug and Play adapter. As an alternative, the oscilloscope may have an integral computer that is capable of carrying out all of the necessary computational functions that will be described below.

A computer 60 is preferably one that is capable of receiving the signal from the oscilloscope 50 and storing the waveforms for future reference and also of comparing the waveforms against reference scans and other standards. It is also preferred that the computer be capable of performing the derivation of the size, concentration and size distribution of particles from an acoustic speckle signal of the particles in a fluid; of determining the degree of asphaltene agglomeration in a hydrocarbon liquid and to initiate any desired alarm or control action. It is more preferred that the computer is programmed with one or more algorithms that are capable of relating the magnitude and/or duration of acoustic speckle signals to the size, concentration, and/or size distribution of the particles in the fluid. The algorithms can include a diffusion model that is capable of relating the size of particles that participate in a speckle event to the duration of an acoustic speckle signal of the speckle event. As an alternative, the algorithm can be one that includes an autocorrelation model that is capable of relating the size of particles that participate in a speckle event to the duration of an acoustic speckle signal of the speckle event.

While the type and computational speed of the computer are not critical, it is preferred that a personal computer having at least a Pentium® processor, or its equivalent, and having spreadsheet software such as, for example, Microsoft Excel®, be used in the present system.

As briefly described above, the present invention provides a novel method for determining the size, concentration and size distribution of particles in a fluid. The method will now be described in more detail.

Figure 5:
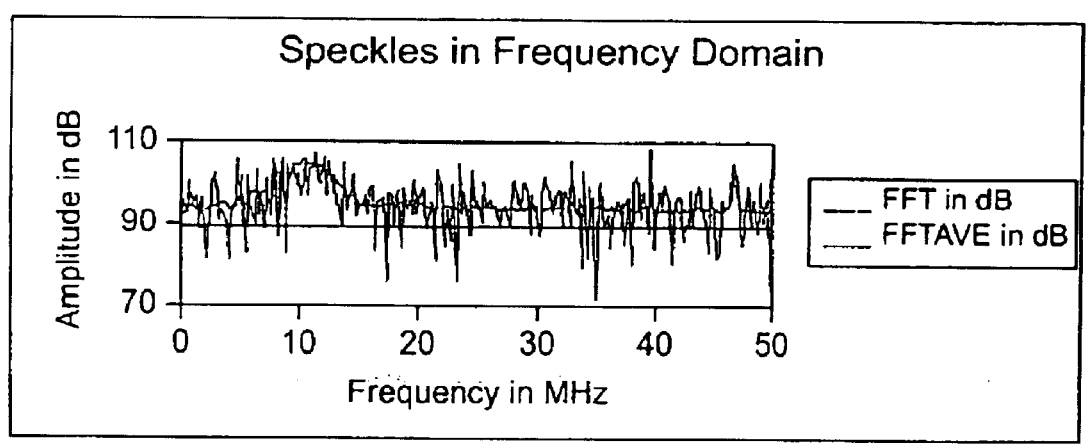
FIG. 5 is a plot of an acoustic speckle signal from crude oil after transformation by Fast Fourier Transform (FFT) into magnitude versus frequency domain, and of the same type of FFT data averaged over time, wherein an acoustic speckle peak is apparent at a frequency of about 10–12 MHz, which is the frequency of the exciting transducer.

The steps of the method include obtaining an acoustic speckle signal of the particles in the fluid and deriving the size, concentration and/or size distribution of the particles from the acoustic speckle signal. One embodiment of the method for obtaining an acoustic speckle signal of the particles in a fluid is by introducing an input signal of acoustic energy into the fluid; sensing a portion of scattered acoustic energy resulting from interaction of the particles with the input signal; producing an output signal corresponding to amplitude of the portion of scattered acoustic energy as a function of time; and transforming the output signal from a time domain to a frequency domain. A peak on the magnitude versus frequency plot, as shown in FIG. 5, can be identified as characteristic of the acoustic speckle. If the transformed output signal is averaged over a period of time that includes two or more speckle events, the coherent scattered acoustic energy will sum, the incoherent scattered acoustic energy will cancel out and a clearer acoustic speckle signal peak can be identified as shown by the less noisy line in FIG. 5.

The output signal that the oscilloscope receives is in an amplitude versus time domain. If it is desired, the output signal can be limited to a certain frequency range before it is transmitted to the oscilloscope in order to delete high frequency signals that provide no information about the particles in the fluid. In some situations, for example, the output signal can be limited to a frequency range of from 1 to 30 MHz, or even from 1 to 20 MHz.

Figure 6A:
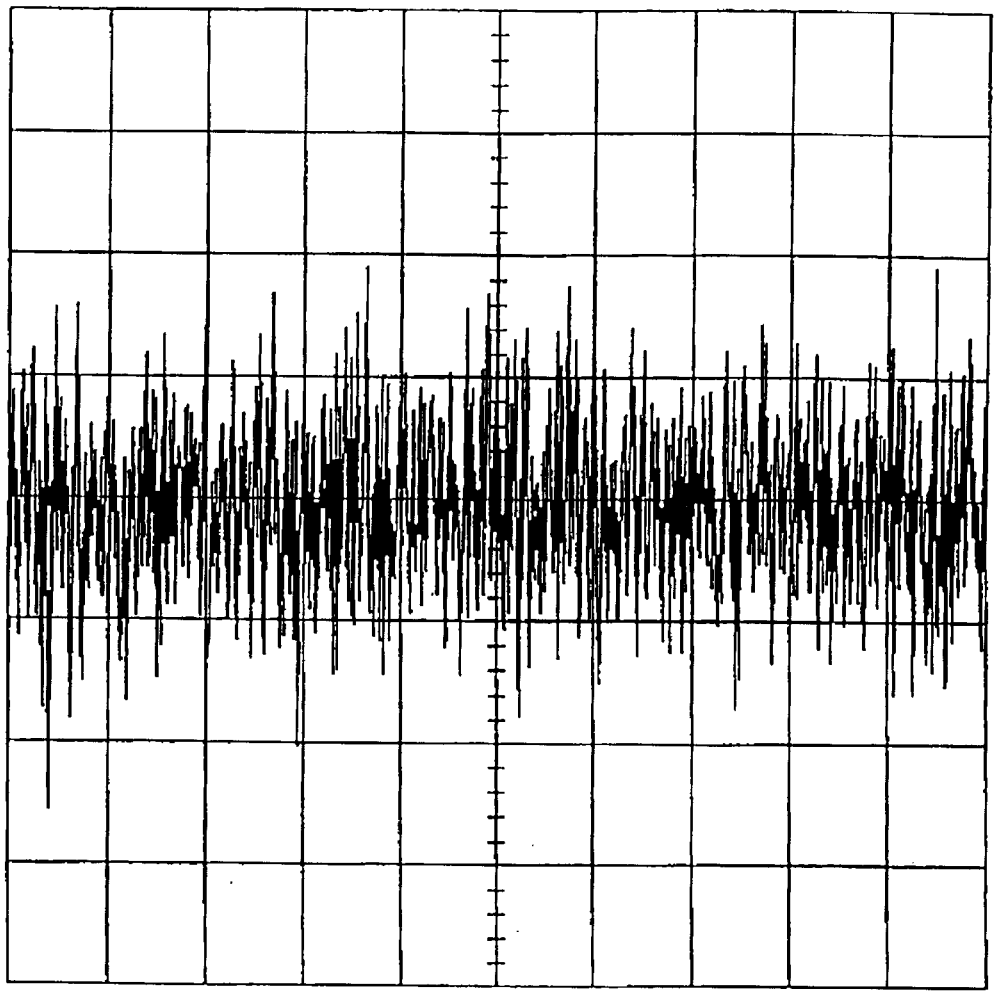
FIG. 6 is a series of plots representing an oscilloscope screen displaying a typical scattered acoustic energy signal from crude oil during several steps of the method of the invention, where 6(a) shows the amplitude of sensed scattered acoustic energy in a time domain; 6(b) shows the amplitude of sensed scattered acoustic energy in a time domain and indicating the selection of that portion of the signal emanating from the focal region as a bolded portion of the signal; 6(c) shows the selected amplitude versus time signal of the signal of 6(b) after Fast Fourier transformation into a frequency domain; and 6(d) is a display of the average of the Fast Fourier Transformed signal in a frequency domain over 900 sweeps with identification of a speckle peak as the broad peak on the left side of the display.
Figure 6B:
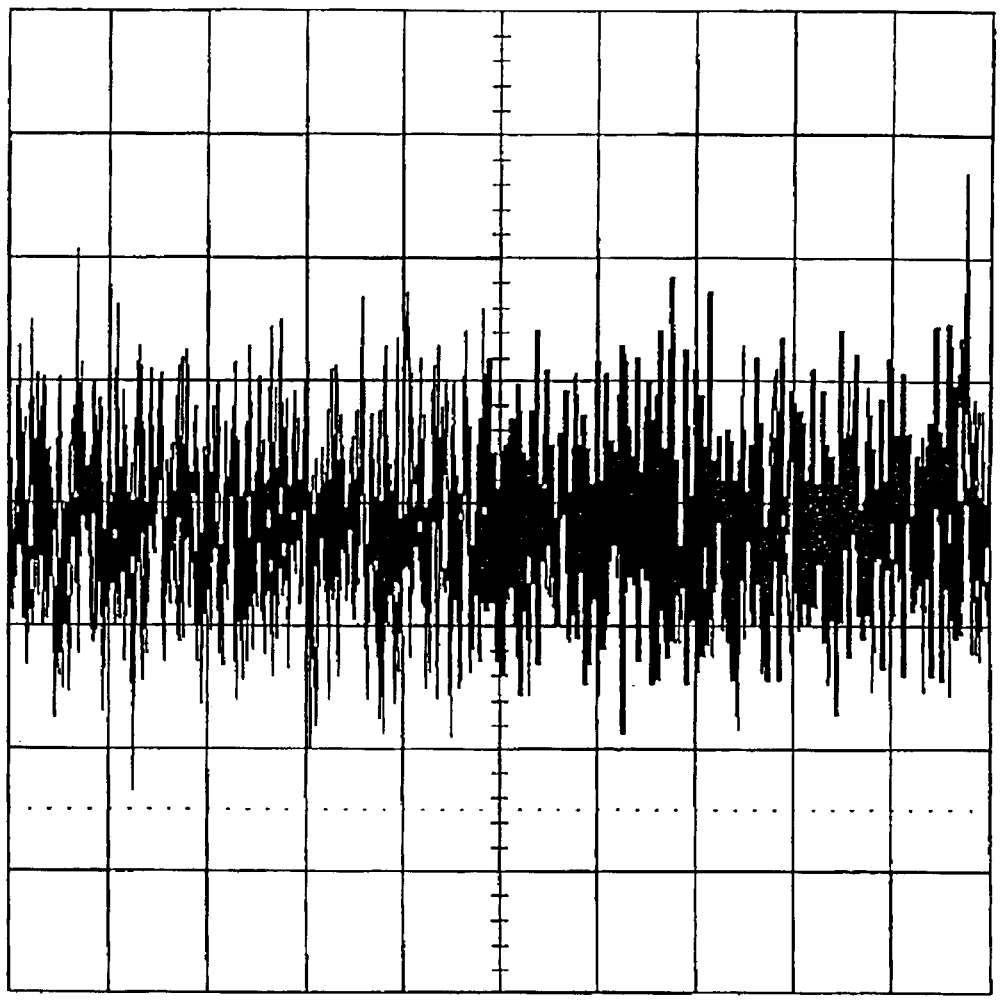

An example of an amplitude versus time signal on an oscilloscope for a sample of crude oil is shown in FIG. 6(a). In order to enhance the detection of acoustic speckle events, the output signal can be limited to acoustic energy scattered by particles in the focal region. FIG. 6(b) shows another oscilloscope plot of an amplitude versus time output signal for crude oil that has been gated, or limited, to the signal from particles in the focal region. The selected part of the signal from the focal region is shown as a bolded section of the signal plot.

The output signal from the focal region is then transformed from a time domain to a frequency domain. This transformation is preferably carried out by the oscilloscope by using a Fast Fourier Transformation (FFT) algorithm to transform the gated signal from time to frequency domain. Computation of the FFT is described in detail at pages C-3 to C-5 of the Operating Manual for the LeCroy Oscilloscope, LeCroy Corporation, Chestnut Hill, N.Y. Where a semiquantitative and simple assessment of the total backscattering is required, the power spectrum can be used. This provides a measure of the total backscattered intensity detected in the focal region.

Figure 6C:
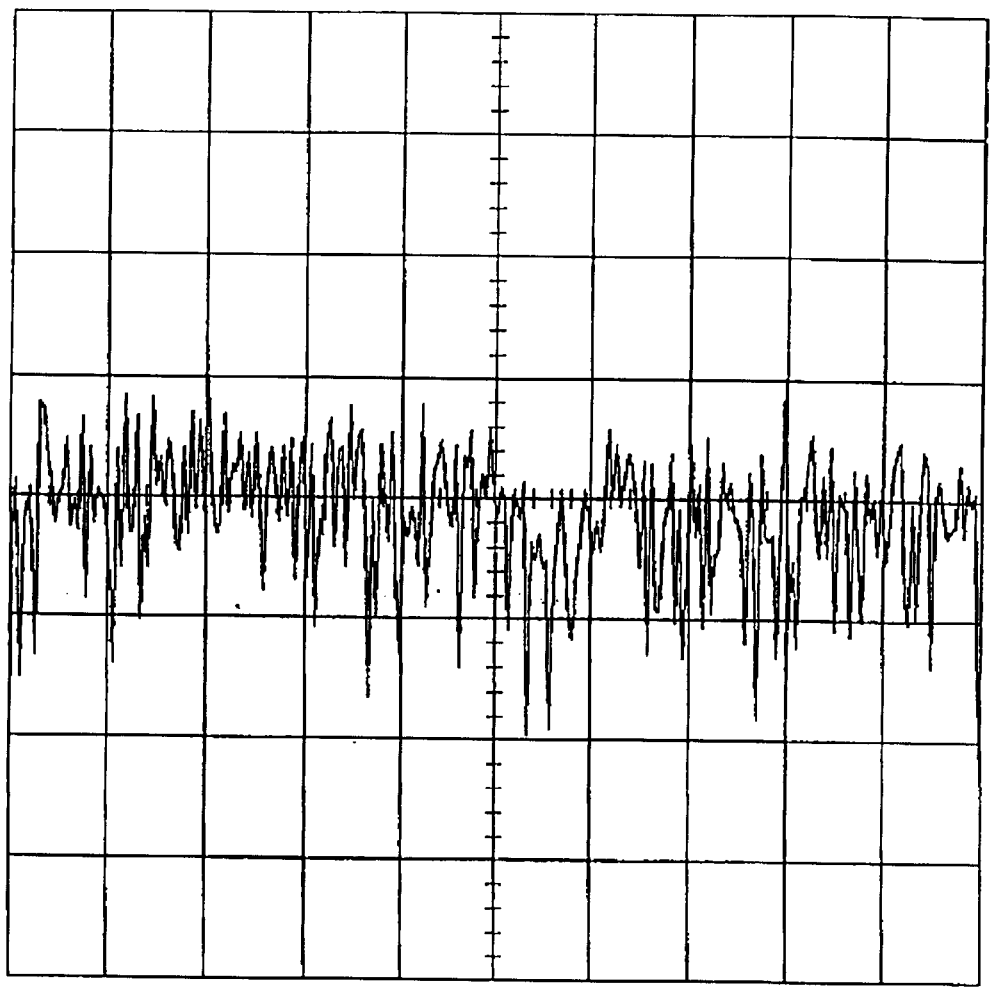
Figure 6D:
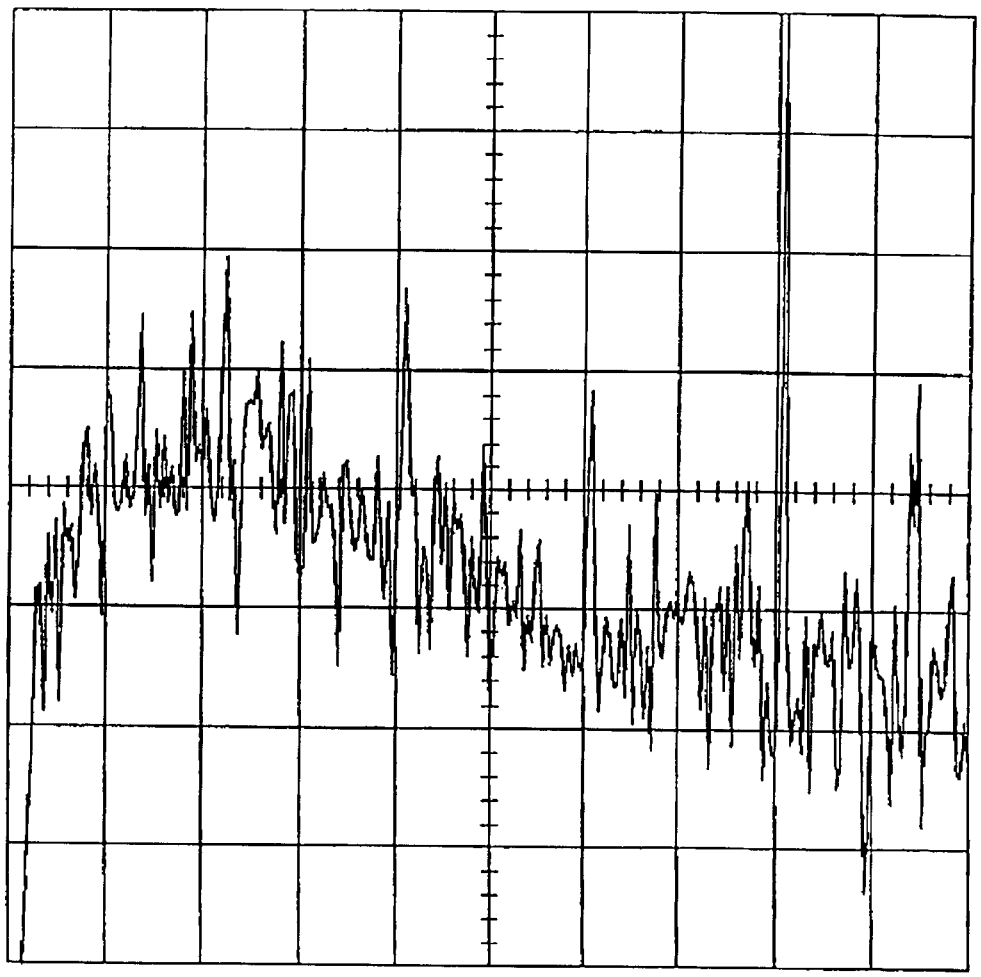

FIG. 6(c) shows the oscilloscope plot of the FFT of the output signal of FIG. 6(b). FIG. 6(d) shows a plot of the FFT of the gated part of the transformed signal averaged over 900 oscilloscope sweeps. The time-averaged acoustic speckle signal is identified on the plot of FIG. 6(d) as the peak at a frequency of about 10 MHz—corresponding to the transducer output maximum.

As described previously, it is believed that the acoustic speckle signal for each individual speckle event has a certain duration that corresponds to the average size of the particles that produced the speckle event. Once the duration of an individual acoustic speckle event is measured, the duration can be used to derive the size of the particles that produced the speckle event. One method for estimating particle size from the duration of the acoustic speckle signal is by the use of an algorithm derived on the basis of a simple diffusion model, such as:

$$t_o = (\lambda/8)^2/2D \qquad \text{Equation 1}$$

where:

$t_o$ is the duration of the acoustic speckle and is the estimated time for dephasing of a acoustic mirror, in seconds. For this estimate the dephasing time is computed to be the time necessary for two particles to move ⅛ of a wavelength in opposite directions;

$\lambda$ is the acoustic wavelength in meters; and

D is the diffusion coefficient, in $m^2s^{-1}$, and is $$D = kT/6\pi\eta a \qquad \text{Equation 2}$$

where:

k is the Boltzman constant ($JK^{-1}$), ($1.38 \times 10^{-23}$);

T is the absolute temperature in degrees Kelvin;

$\pi$ is 3.14159;

$\eta$ is the viscosity of the fluid in Pa·s; and a is the particle radius in meters;

Thus, by combining the two equations and solving for the particle radius (a), the particle size can be calculated for each measurement of acoustic speckle duration ($t_o$).

An alternative, and more accurate, diffusion model that can also be used for deriving particle size from a measurement of the duration of the speckle event is:

$$a = (t_m)(4 \, kT/6\pi\eta)(8/\lambda erfc(1))^2 \qquad \text{Equation 3}$$

where:

a is the particle radius in meters;

$t_m$ is the duration of an acoustic speckle event in seconds; and other parameters are as defined above.

As an alternative to deriving particle size from the duration of an acoustic speckle by using a diffusion model, the particle size can also be derived by using an autocorrelation model of the type described by Berry et al., in *Physical Chemistry*, p.1106, Wiley Publ. New York (1980); and by Wellstead, P. E., *Methods and Applications of Digital Spectral Techniques*, Technical Report No. 0008/83, UMIST, Solartron Instruments, Farnborough, U.K.

Since the novel method measures the average size of particles that produce an individual speckle event, it is believed that when the duration of two or more speckle events are measured, the average particle size that is calculated for the different speckle events will vary within the range of the actual range of sizes of particles in the fluid. It follows that the higher the concentration of particles of a given size, the more frequently those particles will produce speckle events. Thus, the concentration of particles of a given size can be obtained by measuring the frequency of occurrence of speckle events produced by particles having that given size. If desirable, one of ordinary skill would easily be able to obtain a correlation between particle size and frequency of occurrence of speckle events in a fluid having a given viscosity by carrying out a routine test in the same fluid with particles of known size at several concentration levels.

Figure 7:
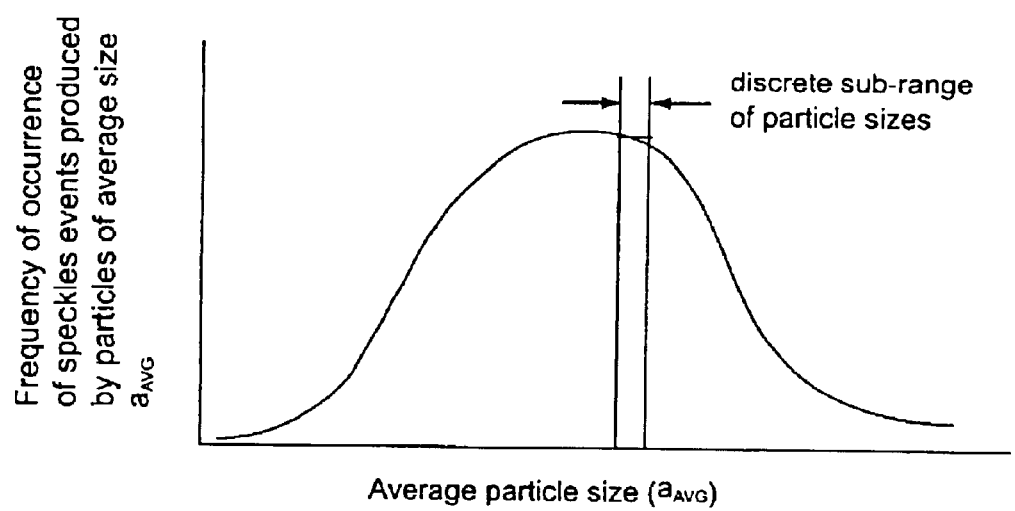
FIG. 7 is a representation of a plot of the frequency of occurrence of speckle events produced by particles having an average size of $a_{AVG}$ versus the average size of particles ($a_{AVG}$) including one sub-range region.

The novel method is capable of making acoustic speckle measurements very rapidly and many speckle events can be recorded and measured within a short period of time. If a sufficient number of individual measurements are taken, the concentration of particles having average sizes that span the size range of all particles in the fluid can be obtained. This can be done by combining the particle concentration measurements for all of the average particle sizes measured. One method for making this combination, for example, is by defining the total range of particle sizes in the fluid as being the range between the smallest and the largest average particle size calculated in the test; dividing the total range of particle sizes into a discrete number of smaller size ranges; and adding together the particle concentrations that were determined for particles having an average size within each smaller size range. For example, if the smallest and largest average particle sizes that were reported in the test were 1 micron and 100 microns, respectively, the total range of particle sizes in the fluid would be taken to be from 1 to 100 microns. This range could then be divided into almost any number of smaller size ranges—20 for example. Each of the 20 smaller size ranges would, in this example, then include all particles of a size within a range of 100/20=5 microns. Thus, the discrete sub-ranges would be 0–5 microns, 5–10 microns, and so on, up to 95–100 microns. An example of how such a plot of frequency of occurrence versus average particle size might appear for this example is shown in FIG. 7. The concentration of particles in the fluid could then be derived by adding the concentration of particles in each of the 20 discrete smaller size ranges.

In fact, by using a similar concept, the novel method makes it possible to derive the particle size distribution in the fluid from a frequency of occurrence versus average particle size distribution. Although only two or more of the particle size measurements are required for such derivation, it is preferred that many individual measurements be used. By way of example, if 2000 individual speckle events are measured over a period of 0.01 second, the 2000 speckle events can be categorized into a number of discrete average particle sizes, each discrete size having a narrow size range. The frequency of occurrence of speckle events in each discrete size range is then essentially a measure of the size distribution of the particles in the fluid. In this case, the distribution measurement would have been provided in the short span of only about 0.01 seconds. This rapidity of measurement provided by the present invention would permit measurement and reporting of particle size distribution on a real-time basis.

To obtain an accurate particle size distribution, a sufficient number of particle size calculations are obtained for the calculation of a particle size distribution for the particles in the fluid. If the plot of FIG. 7, for example, is based on a sufficient number of individual particle size calculations, the curve itself would be indicative of the particle size distribution. It is preferred that the size distribution be derived on the basis of at least about 100 individual particle size calculations and at least about 500 individual calculations are more preferred, at least about 1000 individual calcula-tions are even more preferred, and at least about 2000 calculations or more are most preferred. It is also necessary to presume a particular form for the particle size distribution, such as, for example, a log-normal distribution.

An alternative method for the calculation of the concentration of particles in a fluid comprises determining the size of the particles in the fluid from the duration of speckles as described previously—for example, by calculating the average radius (a)—and then determining the total cross-section area of particles in the focal region ($A_{fr}$). It is believed that the maximum magnitude (maximum peak height; H) of each individual speckle signal is directly proportional to the total cross-section area of the particles that produced the speckle event. Thus, by assuming that each particle has a certain geometry (namely spherical), the total cross-section area of the particles that produced the individual speckle event can be correlated with the maximum magnitude of the individual speckle signal as:

$$A_{fr} = c(H) \qquad \text{Equation 4}$$

where:

c is a proportionality constant; and

H is proportional to the maximum peak height, or magnitude, of the individual speckle signal.

A representative volume can be defined as being the volume of fluid within the focal region ($V_{fr}$). If it is assumed that the particles that are within this volume are the particles that produce the acoustic speckle events that are being measured, then the concentration of particles in the focal volume can be derived from the volume of the focal region and the particle sizes and total-cross section area of particles measured as:

$$n/V_{fr} = A_{fr}/\pi a^2 V_{fr} \qquad \text{Equation 5}$$

where:

$n/V_{fr}$ is the number of particles in the focal volume; and other parameters are as defined previously.

If the concentration of particles in the focal region is measured for two or more speckle events and the values of such concentrations are averaged, the concentration of particles in the fluid can be calculated. As described previously, it is preferred that measurements be taken for many speckle events in order to increase the accuracy of the calculation.

For purposes of increasing speed and simplicity of the method, the step of calculating particle concentration from speckle peak height can be left out and a value that is proportional to particle concentration can be calculated directly from average particle size and speckle peak height data.

Once the concentration of particles of a given average size has been calculated by either method, the size distribution of particles in the fluid can be calculated as described previously.

The apparatus and method of the present invention can be used to measure the size, concentration and size distribution of particles in any fluid, but the novel apparatus and method are particularly useful for use where the fluid is a liquid and even more particularly when the liquid is an optically opaque liquid. The novel apparatus and method can be used when the liquid is corrosive, hot or under pressure. A particularly useful application of the subject method and apparatus is for the measurement of particles in crude oil, or other opaque hydrocarbon liquids.

One embodiment of the novel method has been found to be particularly useful for determining the degree of agglomeration of small particles, such as asphaltene particles, in liquids. This embodiment is especially useful when the liquid is a hydrocarbon liquid. This method comprises obtaining, for two or more individual speckle events, an individual acoustic speckle signal from the hydrocarbon liquid and determining the degree of asphaltene agglomeration from the acoustic speckle signal.

In particular, an input signal of acoustic energy is introduced into the fluid, which input signal is focused on a focal region in the liquid. An output signal of the acoustic energy that is scattered by the particles in the focal region in response to their interaction with the input signal is sensed as amplitude as a function of time. This output signal is then transformed from a time domain to a frequency domain. As described above, the transformation is preferably carried out by an the oscilloscope by the use of a Fast Fourier Transform algorithm. An acoustic speckle signal from the transformed output signal in the frequency domain is then identified.

It should be emphasized that the common practice of averaging the instantaneous input signal will not work for the subject method, because the total of speckle events sums to zero and all information that can potentially be derived from the speckle is lost. It is believed that this occurs because each speckle event occurs at a slightly different position in space. Thus, averaging of the backscattered signal can only be carried out after the instantaneous signal amplitude versus time plot has been transformed into the frequency domain.

Figure 8:
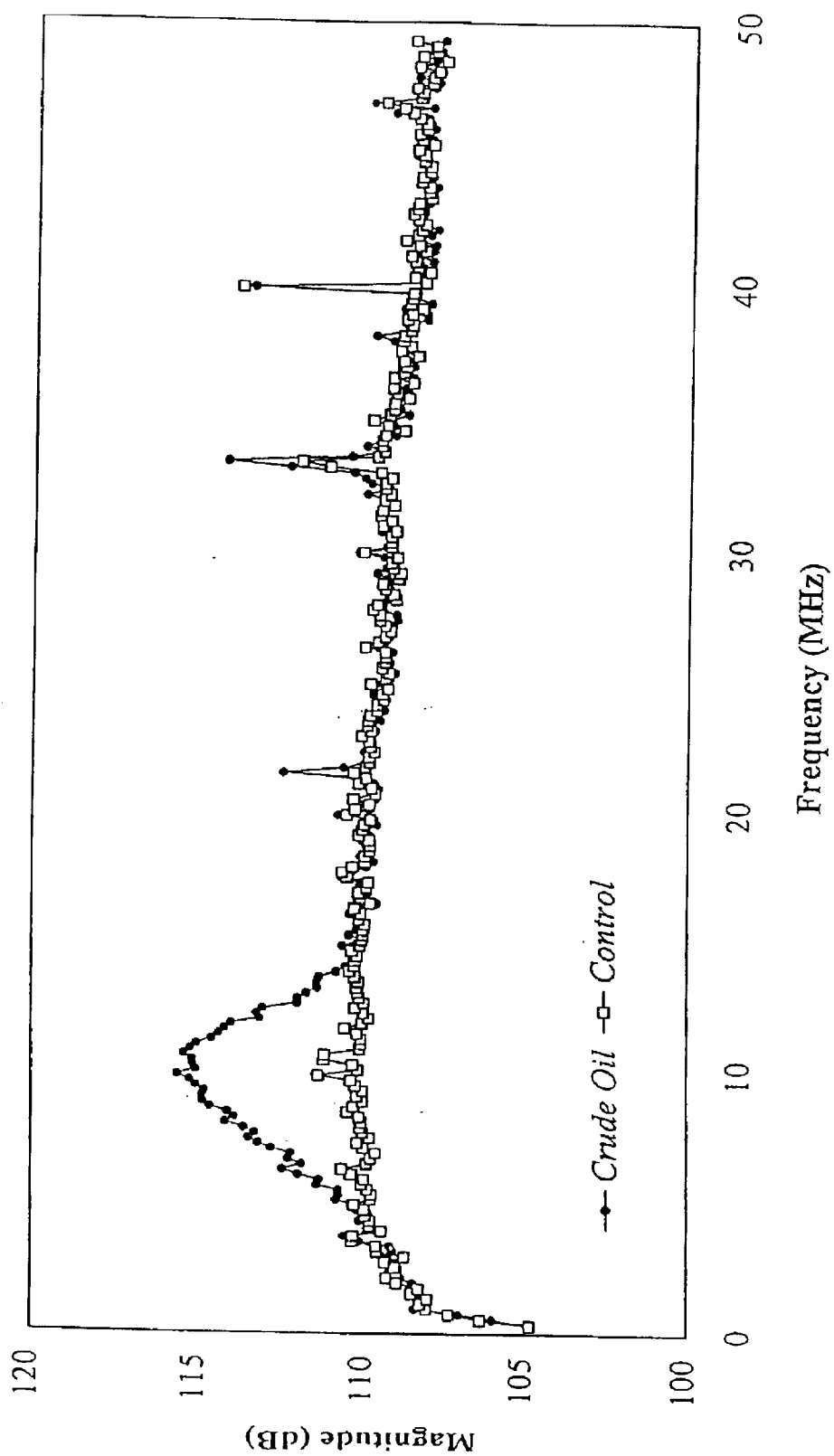
FIG. 8 shows an oscilloscope display of an averaged transformed output signal from a crude oil sample that has a speckle peak at a frequency of about 10–12 MHz superimposed with an averaged transformed output signal from a control fluid—n-heptane.

Each of these steps is then repeated, but in a control liquid that contains no asphaltene particles. The transformed signal from the control liquid acts as a baseline standard. A plot of a transformed output signal from a crude oil sample plotted concurrently with a transformed signal from n-heptane as a control fluid is shown in FIG. 8. The degree of asphaltene agglomeration can be determined by comparing the acoustic speckle signal from the hydrocarbon liquid with the acoustic speckle signal from the control liquid.

Figure 9:
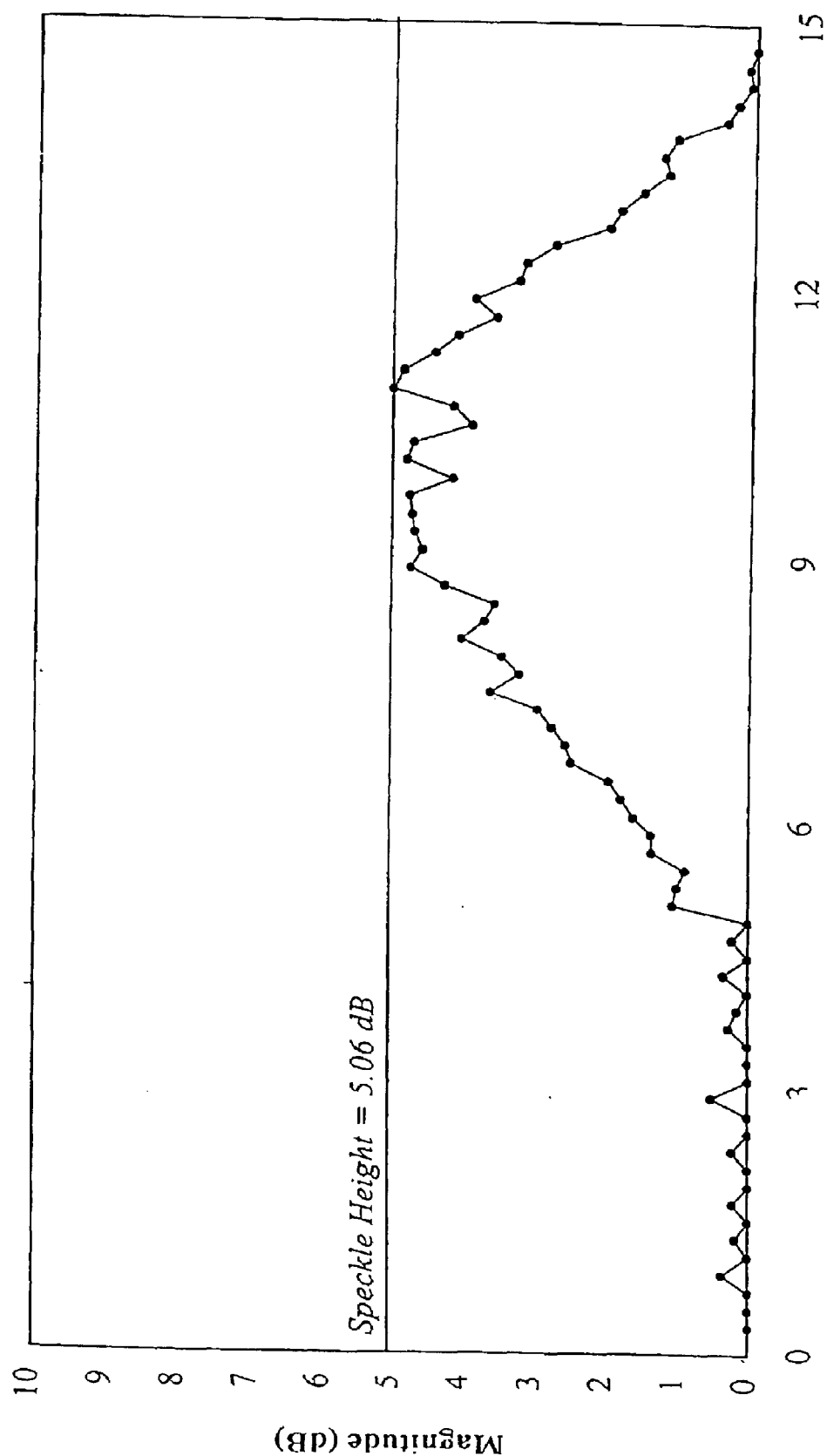
FIG. 9 shows a plot of speckle height that is derived from the difference between the averaged transformed output signals shown in FIG. 8.

One method by which the signal from the hydrocarbon liquid and the sample from the control liquid can be compared is by subtracting the magnitude of the acoustic speckle signal of the hydrocarbon liquid at a selected frequency from the magnitude of the acoustic speckle signal of the control liquid at the same frequency to obtain a difference. The maximum value of this difference between the two curves is herein termed the "speckle height". An illustration of the calculation of the speckle height from the data of FIG. 8 is shown in FIG. 9, where maximum speckle height is seen to occur at a frequency of about 11 MHz.

The method and apparatus of the present invention can be used when the test fluid is static, such as in a non-flow sample cell, but it can also be used in an agitated tank or process line in which the fluid is flowing. The only limitation for the use of the method in a flow situation is that the particles constituting the speckle mirror remain illuminated by the acoustic beam throughout the speckle event. Thus, flow along the acoustic beam axis will remain longer in the beam than flow transverse to the beam. In practice, the longest event that can be detected will be a function of beam width, flow rate, the size of the focal region and the relationship between the direction of fluid flow and the acoustic beam direction. Transducers that are installed in an elbow of a flow conduit and which have their beam aligned into the incoming or outgoing fluid, for example, would be preferred for use in fluid flow situations.

The present method and apparatus have the advantage of being useable with only one transducer when it is important to minimize cost or number of penetrations into the fluid. Only a single type of signal is required—an acoustic energy signal—rather than requiring other, additional signals and there is no need for the addition of titrants, such as heptane or hexane, or contaminating chemicals to the subject fluid. Measurements by the present method and apparatus provide a measurement of particle size, concentration and/or size distribution that are available very quickly and even on a real-time basis.

The following examples describe the preferred embodiments of the invention. Other embodiments within the scope of the claims herein will be apparent to one skilled in the art from consideration of the specification or practice of the invention as disclosed herein. It is intended that the specification together with the examples, be considered exemplary only, with the scope and spirit of the invention being indicated by the claims which follow the examples.

EXAMPLE 1

This example shows the observation of acoustic speckle in crude oil.

A SLIM 10-10/SF30 mm/834/02 transducer, available from Sonatest, UK; Dickens Road, Milton Keynes, MK12 5QQ, UK; was connected with a pulser/receiver and a LeCroy 9310A oscilloscope as shown in FIG. 3. The transducer also acted as the sensor for backscattered acoustic energy. The input signal settings were 500 volts, 25 ns, 200 Hz and using a power receiver having a gain of 33 dB. The oscilloscope settings were set to an impedance of DC50 Ohms, with the screen plot axes being set to 0.5 microseconds per division for the X-axis (time) and from 5 mV to 20 mV per division (amplitude) for the Y-axis.

The tip of the transducer was immersed into a sample of crude oil at 23° C. in a test cell and the input signal and sensing of the scattering was started. The delay time required for the input signal to move to the focal region and the backscattered acoustic energy to move back to the transducer was 41.5 microseconds+0.5 microseconds/division×5 divisions.

The backscattered signal received by the transducer was gated to the focal region and transformed by the oscilloscope by using a Fast Fourier Transform from a time domain to a frequency domain. The FFT transformed signal was averaged over 435 sweeps and the magnitude of the resulting averaged transformed signal was plotted versus frequency. A peak was seen which had a maximum magnitude at about 10–12 MHz. This peak was identified as being the "speckle peak". It is believed that the peak is the image in the frequency domain of the acoustic transducer output.

EXAMPLE 2

This example illustrates the calculation of particle size as a function of the duration of an acoustic speckle by the use of two diffusion models. The first model is a simple calculation, but provides a less accurate value than the second model. The physical constants for asphaltene particles in crude oil were estimated and used for the computation for both models. The second model is used to show the dependence of the calculated particle size on the viscosity of the fluid.

| PARAMETER | UNITS | SYMBOL | VALUE | FORMULA OR COMMENTS |
|---|---|---|---|---|
| | | Definition of variables | | |
| Boltzman constant | J K$^{-1}$ | k | $1.38 \times 10^{-23}$ | |
| Temperature | °C. | | 25 | Ambient |
| Absolute temperature | K. | T | 298.15 | |
| Viscosity | Pa · s | $\eta$ | $7.00 \times 10^{-3}$ | Figure for low viscosity fraction |
| Particle Radius | m | a | $1.00 \times 10^{-8}$ | Figure for asphaltenes |
| Particle Diameter | m | d | $2.00 \times 10^{-8}$ | =2a |
| Particle density | kg m$^{-3}$ | $\rho$ | $1.00 \times 10^{3}$ | Guess |
| Particle Mass | kg | m | $4.19 \times 10^{-24}$ | $=\frac{4}{3}\pi a^3 \rho$ |
| Velocity of sound | m s$^{-1}$ | v | 1200 | Approximate figure for crude oil |
| Frequency of sound | Hz | f | $1.00 \times 10^{7}$ | Sonatest transducer |
| Wavelength | m | $\lambda$ | $1.2 \times 10^{-4}$ | |
| Computed values of the duration of a speckle event for a particle with radius of $10^{-8}$ m | | | | |
| Mobility coefficient[a] | s kg$^{-1}$ | $\mu$ | $2.50 \times 10^{9}$ | =50/d |
| Diffusion coefficient | m$^2$ s$^{-1}$ | D | $3.12 \times 10^{-12}$ | $=\frac{kT}{6\pi\eta a}$ |
| Time interval[b] | s | $t_0$ | 36.1 | $=(\lambda/8)^2/2D$ |
| A more accurate version of a diffusion model can be formulated as shown below: | | | | |
| Time correction | s | $t_{corr}$ | $-1.05 \times 10^{-11}$ | $=-m\mu + \exp(-t_0/m\mu)$ |
| Einstein condition[c] ($t_0 \gg m\mu$) | m*$\mu$ | | $1.05 \times 10^{-11}$ | $=m\mu$ |
| Time corrected diffusion coefficient[d] | m$^2$ s$^{-1}$ | D(t) | $3.12 \times 10^{-12}$ | $=D(1 - (t_{corr}/m\mu))$ |
| The above three lines are checks on the validity of the Einstein condition and include on the final line a corrected version of the diffusion coefficient in the case that the Einstein condition fails. This is not needed in the example calculation given here but can be necessary under some conditions. | | | | |
| Distance moved in time interval[e] | m | <r> | $2.37 \times 10^{-7}$ | $=3(2Dt_0)^{0.5}$ |
| Period | s | T(f) | $1.0 \times 10^{-7}$ | |
| Time for a step change in concentration to reduce to 50% over a distance of $\lambda/8$ | s | $t_{mirror}$ | 0.446 | $=((\lambda/8)erfc(1))^2/4D$ |
| The above is a more accurate calculation of the time taken for the particle mirror to break up due to diffusion. It agrees very well with experimental observations and with what is known about the size of asphaltene particles. | | | | |

[a]Dickinson, E. and McClements, D. J., "Advances in Food Colloids", Blackie, 1995, p126, equation 4.25, estimate for particle in water. Here it is assumed that the diffusion of asphaltenes is similar to that of particles in water.
[b]This is the condition for the de-phasing of the mirror. It is derived from the Einstein equation for the average displacement of a given particle in a one-dimensional projection (Einstein, 1905), and see reference above, page 125, equation 4.23. The condition for de-phasing of the mirror is that particles need only move ⅛ of a wavelength. A movement of one-half of a wavelength is necessary for complete phase cancellation. However, at least two particles must be involved and they can move in opposite directions. So a movement of one-eighth of a wavelength on the part of two particles moving in opposite directions, along the transducer axis, will result in a substantial reduction of the phase of the mirror.
[c]Equation 4.25 in Dickinson, E. and McClements, D. J., "Advances in Food Colloids", Blackie (1995).
[d]This is a different way of writing Equation 4.25 in Dickinson and McClements, Id.
[e]This is computed from the Einstein equation for motion in 3 dimensions. $<r^2> = 3<x^2>$
The viscosity of water is assumed to be 0.008 Pa · s; and the viscosity of sunflower oil is 0.05 Pa · s.

The table below is in three parts. The first section of the table shows the effect of variation in the viscosity of the fluid on the particle size calculation. The second section of the table shows the dependence of the duration of an acoustic speckle on particle size at a single value of viscosity. The third part of the table shows the calculation of particle size as a function of the duration of an acoustic speckle by a diffusion model.

| Dependence of $t_{mirror}$ on $\eta$ | | | |
|---|---|---|---|
| $\eta$ | $t_{mirror}$ | D | a |
| 0.0001 | 0.006376 | $2.18279 \times 10^{-10}$ | $1.00 \times 10^{-8}$ |
| 0.001 | 0.063762 | $2.18279 \times 10^{-11}$ | $1.00 \times 10^{-8}$ |
| 0.01 | 0.637622 | $2.18279 \times 10^{-12}$ | $1.00 \times 10^{-8}$ |
| 0.1 | 6.376218 | $2.18279 \times 10^{-13}$ | $1.00 \times 10^{-8}$ |

-continued

Dependence of $t_{mirror}$ on a

| a | $t_{mirror}$ | D | η |
|---|---|---|---|
| $1.00 \times 10^{-8}$ | 0.446335 | $3.12 \times 10^{-12}$ | $7.00 \times 10^{-3}$ |
| $1.00 \times 10^{-7}$ | 4.463352 | $3.12 \times 10^{-13}$ | $7.00 \times 10^{-3}$ |
| $1.00 \times 10^{-6}$ | 44.63352 | $3.12 \times 10^{-14}$ | $7.00 \times 10^{-3}$ |
| $1.00 \times 10^{-5}$ | 446.3352 | $3.12 \times 10^{-15}$ | $7.00 \times 10^{-3}$ |
| $1.00 \times 10^{-4}$ | 4463.352 | $3.12 \times 10^{-16}$ | $7.00 \times 10^{-3}$ |
| $1.00 \times 10^{-3}$ | 44633.52 | $3.12 \times 10^{-17}$ | $7.00 \times 10^{-3}$ |

Dependence of a on $t_{mirror}$

| $t_{mirror}$ (sec) | a (meters) |
|---|---|
| $1.00 \times 10^{-4}$ | $2.24 \times 10^{-12}$ |
| $1.00 \times 10^{-3}$ | $2.24 \times 10^{-11}$ |
| $1.00 \times 10^{-2}$ | $2.24 \times 10^{-10}$ |
| $1.00 \times 10^{-1}$ | $2.24 \times 10^{-9}$ |
| 1 | $2.24 \times 10^{-8}$ |
| 10 | $2.24 \times 10^{-7}$ |
| 100 | $2.24 \times 10^{-6}$ |

$a = t_{mirror} (4kT/6\pi\eta)((8/\lambda erfc(1))^2)$

All references cited in this specification, including without limitation all journal articles, brochures, manuals, periodicals, texts, manuscripts, website publications, and any and all other publications, are hereby incorporated by reference. The discussion of the references herein is intended merely to summarize the assertions made by their authors and no admission is made that any reference constitutes prior art. Applicants reserve the right to challenge the accuracy and pertinence of the cited references.

In view of the above, it will be seen that the several advantages of the invention are achieved and other advantageous results are obtained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for determining the size distribution of particles in a fluid comprising the steps of obtaining an acoustic speckle signal of the particles in the fluid and deriving the size distribution of the particles from the acoustic speckle signal.

2. The method as set forth in claim 1, wherein the acoustic speckle signal is obtained by introducing an input signal of acoustic energy into the fluid; sensing a portion of scattered acoustic energy resulting from interaction of the particles with the input signal; producing an output signal corresponding to amplitude of the portion of scattered acoustic energy as a function of time; transforming the output signal from a time domain to a frequency domain; and identifying the acoustic speckle signal from the output signal transformed to the frequency domain.

3. The method as set forth in claim 2, wherein the input signal is focused on a focal region in the fluid and some of the input signal is scattered by particles in the focal region, and wherein the output signal is limited to the portion of acoustic energy scattered by particles in the focal region.

4. The method as set forth in claim 3, wherein the fluid contains particles that produce individual speckle events and wherein the size distribution of the particles in the fluid is derived by calculating, for two or more individual acoustic speckle events, the size of the particles that produced each individual speckle event; measuring the frequency of occurrence of speckle events that were produced by particles having the same size; and deriving the particle size distribution from the frequency of occurrence of speckle events as a function of particle size.

5. The method as set forth in claim 4, wherein a sufficient number of particle size calculations are obtained for the calculation of a particle size distribution for the particles in the fluid and wherein the size distribution of particles in the fluid is determined as the frequency of occurrence of acoustic speckle events produced by particles having a certain size.

6. The method as set forth in claim 5, comprising at least about 100 particle size calculations.

7. The method as set forth in claim 6, comprising at least about 500 particle size calculations.

8. The method as set forth in claim 7, comprising at least about 1000 particle size calculations.

9. The method as set forth in claim 8, comprising at least about 2000 particle size calculations.

10. The method as set forth in claim 4, wherein, for each individual speckle event, the size of the particles that produced that speckle event is derived from the duration of each individual acoustic speckle signal for that individual speckle event by using a diffusion model.

11. The method as set forth in claim 10, wherein the diffusion model is of the form:

$$a=(t_m)(4kT/6\pi\eta)(8/\lambda erfc(1))^2$$

where:

a is the particle radius in meters;

$t_m$ is the duration of an acoustic speckle event in seconds

λ is the acoustic wavelength in meters;

k is the Boltzman constant ($JK^{-1}$), ($1.38 \times 10^{-23}$);

T is the absolute temperature in degrees Kelvin;

π is 3.14159; and

η is the viscosity of the fluid in Pa·s.

12. The method as set forth in claim 4, wherein, for each individual speckle event, the size of the particles that produced that speckle event is derived from the duration of each individual acoustic speckle signal for that individual speckle event by using an autocorrelation model.

13. The method as set forth in claim 4, wherein, for each individual speckle event, the size of the particles that produced that speckle event is derived by measuring the amplitude of the acoustic speckle signal that produced that speckle event and correlating the particle size with the maximum amplitude of such acoustic speckle signal.

14. The method as set forth in claim 3, where the fluid contains particles that produce individual speckle events and wherein the size distribution of the particles in the fluid is determined from the acoustic speckle signal by, for each of two or more individual speckle events, identifying an individual acoustic speckle signal corresponding to the individual speckle event; measuring the duration of the individual acoustic speckle signal; deriving the size of the particles that produced the individual speckle event from the duration of the individual acoustic speckle signal, determining the volume of the focal region; calculating the concentration of particles having the size of those that produced the individual speckle event from the particle size and the volume of the focal region, and determining the size distribution of particles in the fluid from the particle size and concentration as measured for the two or more speckle events.

15. The method as set forth in claim 14, wherein, for each individual speckle event, the size of the particles that produced that speckle event is derived from the duration of the individual acoustic speckle signal for that individual speckle event by using a diffusion model.

16. The method as set forth in claim 14, wherein, for each individual speckle event, the size of the particles that produced that speckle event is derived from the duration of the individual acoustic speckle signal for that individual speckle event by using an autocorrelation model.

17. The method as set forth in claim 14, wherein, for each individual speckle event, the size of the particles that produced that speckle event is derived by measuring the amplitude of the individual acoustic speckle signal and correlating the particle size with the maximum amplitude of such individual acoustic speckle signal.

18. The method as set forth in claim 1, wherein the fluid is a liquid.

19. The method as set forth in claim 18, wherein the liquid is a liquid hydrocarbon.

20. The method as set forth in claim 19, wherein the liquid hydrocarbon is optically opaque.

21. The method as set forth in claim 20, wherein the liquid hydrocarbon is crude oil.

22. The method as set forth in claim 18, wherein the input signal of acoustic energy is an input signal of ultrasonic energy.

23. The method as set forth in claim 1, wherein the fluid is a liquid hydrocarbon that contains particles that produce individual speckle events by interaction with acoustic energy, and the method comprises the steps of (a) introducing an input signal of acoustic energy into the hydrocarbon, which input signal is focused on a focal region in the hydrocarbon, such that particles in the focal region interact with the input signal to scatter the acoustic energy, producing an output signal of the acoustic energy scattered by the particles in the focal region; (b) sensing the output signal in the form of amplitude as a function of time; (c) transforming the sensed output signal from a time domain to a frequency domain, (d) identifying an acoustic speckle signal from the transformed output signal in the frequency domain; (e) carrying out each of the steps (a), (b), (c) and (d) except on a control liquid that contains no asphaltene particles instead of the hydrocarbon; and (f) determining the size distribution of particles in the hydrocarbon by comparing the acoustic speckle signal derived from the hydrocarbon with the acoustic speckle signal derived from the control liquid.

24. The method as set forth in claim 23, wherein the acoustic speckle signal of the hydrocarbon has a magnitude at each of a plurality of frequencies, including a selected frequency, and the acoustic speckle signal of the control liquid has a magnitude at each of the plurality of frequencies, and the comparison of the acoustic speckle derived from the hydrocarbon is compared with the acoustic speckle signal derived from the control liquid by subtracting the magnitude of the acoustic speckle signal of the hydrocarbon liquid at the selected frequency from the magnitude of the acoustic speckle signal of the control liquid at the selected frequency to obtain a difference.

25. The method as set forth in claim 23, wherein the sensed output signal is transformed from a time domain to frequency domain by use of a Fast Fourier Transform algorithm.

* * * * *